(12) United States Patent
Vicari et al.

(10) Patent No.: US 11,292,717 B2
(45) Date of Patent: Apr. 5, 2022

(54) METHOD FOR PRODUCING METHANOL FROM SYNTHESIS GAS WITHOUT THE EMISSION OF CARBON DIOXIDE

(71) Applicant: BASF SE, Ludwigshafen am Rhein (DE)

(72) Inventors: Maximilian Vicari, Ludwigshafen am Rhein (DE); Thomas Geiger, Ludwigshafen am Rhein (DE); Torsten Katz, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/273,478

(22) PCT Filed: Aug. 26, 2019

(86) PCT No.: PCT/EP2019/072713
§ 371 (c)(1),
(2) Date: Mar. 4, 2021

(87) PCT Pub. No.: WO2020/048809
PCT Pub. Date: Mar. 12, 2020

(65) Prior Publication Data
US 2021/0363007 A1    Nov. 25, 2021

(30) Foreign Application Priority Data
Sep. 4, 2018 (EP) .................................. 18192465

(51) Int. Cl.
*C01B 3/38* (2006.01)
*C07C 29/151* (2006.01)
*C07C 29/80* (2006.01)

(52) U.S. Cl.
CPC .......... *C01B 3/382* (2013.01); *C07C 29/1518* (2013.01); *C07C 29/80* (2013.01);
(Continued)

(58) Field of Classification Search
CPC .............. C07C 29/1518; C07C 29/80; C07C 2523/80; C07C 29/154; C01B 3/382;
(Continued)

(56) References Cited

U.S. PATENT DOCUMENTS 8,829,059 B2    9/2014  Wynn
2008/0236390 A1   10/2008  Anders et al.
(Continued)

FOREIGN PATENT DOCUMENTS

EP    2228358 A1    9/2010
EP    3178804 A1    6/2017

OTHER PUBLICATIONS

International Preliminary Reporton Patentability received for PCT Patent Application No. PCT/EP2019/072713, dated Mar. 18, 2021, 13 pages (8 pages of English Translation and 5 pages of Original Document).

(Continued)

*Primary Examiner* — Jafar F Parsa
(74) *Attorney, Agent, or Firm* — Faegre Drinker Biddle & Reath LLP

(57) ABSTRACT

A process for preparing methanol from a carbon-containing feedstock by producing synthesis gas therefrom in a synthesis gas production unit, converting the synthesis gas to methanol in a methanol synthesis unit and working up the reaction mixture obtained stepwise to isolate the methanol, wherein the carbon monoxide, carbon dioxide, dimethyl ether and methane components of value from the streams separated off in the isolation of the methanol are combusted with an oxygenous gas, and the carbon dioxide in the resultant flue gas is separated off in a carbon dioxide recovery unit and recycled to the synthesis gas production unit and/or to the methanol synthesis unit.

17 Claims, 6 Drawing Sheets

(52) U.S. Cl.
CPC ........... *C01B 2203/0261* (2013.01); *C01B 2203/043* (2013.01); *C01B 2203/0415* (2013.01); *C01B 2203/0475* (2013.01); *C01B 2203/061* (2013.01); *C01B 2203/148* (2013.01); *C01P 2006/82* (2013.01); *C07C 2523/80* (2013.01)

(58) Field of Classification Search
CPC .... C01B 2203/0261; C01B 2203/0415; C01B 2203/0475; C01B 2203/061; C01B 2203/148
See application file for complete search history.

(56) References Cited

U.S. PATENT DOCUMENTS

| | | |
|---|---|---|
| 2010/0192770 A1 | 8/2010 | Andarcia et al. |
| 2011/0094381 A1 | 4/2011 | Lichtfers et al. |
| 2015/0251983 A1* | 9/2015 | Panza .................. C01B 3/38 518/702 |

OTHER PUBLICATIONS

International Search Report and Written Opinion received for PCT Patent Application No. PCT/EP2019/072713, dated Nov. 11, 2019, 15 pages (7 pages of English Translation and 8 pages of Original Document).
International Search Report for PCT Patent Application No. PCT/EP2019/072713, dated Nov. 11, 2019, 3 pages.
Ott, et al., "Methanol", Ullmann's Encyclopedia of Industrial Chemistry, Oct. 15, 2012, pp. 1-27.
Reddy, et al., "Cost Effective CO2 Capture from Flue Gas for Increasing Methanol Plant Production", Energy Procedia, vol. 63, 2014, pp. 1407-1414.
Topham, et al., "Carbon Dioxide", Ullmann's Encyclopedia of Industrial Chemistry, May 30, 2014, pp. 1-43.

* cited by examiner

METHOD FOR PRODUCING METHANOL FROM SYNTHESIS GAS WITHOUT THE EMISSION OF CARBON DIOXIDE

CROSS-REFERENCE TO RELATED APPLICATIONS

This application is a national stage application (under 35 U.S.C. § 371) of PCT/EP2019/072713, filed Aug. 26, 2019, which claims benefit of European Application No. 18192465.5, filed Sep. 4, 2018, both of which are incorporated herein by reference in their entirety.

The present invention relates to a process for preparing methanol from synthesis gas, in which the carbon compounds in the streams separated off in the isolation of the methanol are converted to carbon dioxide and, with avoidance of emission thereof, reused in the preparation of methanol. This process is based on the continuously operated methanol synthesis, known to those skilled in the art, by the low-pressure process.

Methanol is one of the most important synthesis raw materials globally and its uses include not only its use as solvent but also for the syntheses of formaldehyde, acetic acid, methyl tert-butyl ether (MTBE), dimethyl terephthalate, methyl methacrylate and methylamines in large volumes.

Methanol is produced on the industrial scale from synthesis gas in a reactor in the presence of a methanol synthesis catalyst. The synthesis gas comprises mainly hydrogen and carbon monoxide, and, depending on the amount of production and workup, also corresponding amounts of carbon dioxide, water and what are called inert gases, for instance methane, nitrogen or argon.

According to Ullmann's Encyclopedia of Industrial Chemistry, "Methanol" chapter, 2012 Wiley-VCH Verlag GmbH & Co. KGaA, Weinheim, Germany, synthesis gas is converted to methanol typically in what is called the low-pressure process within a pressure range of 5 to 10 MPa abs over copper- and zinc-comprising methanol synthesis catalysts. This involves converting both carbon monoxide and carbon dioxide to methanol.

$$CO + 2H_2 \rightleftharpoons CH_3OH \quad (1)$$

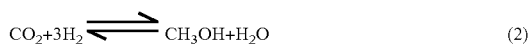

$$CO_2 + 3H_2 \rightleftharpoons CH_3OH + H_2O \quad (2)$$

Based on reaction equations (1) and (2), the stoichiometric number S is found as follows for the methanol synthesis:

$$S = \frac{n(H_2) - n(CO_2)}{n(CO) + n(CO_2)} \quad (3)$$

where n in each case represents the respective molar amounts. A stoichiometric number S of 2 corresponds to the theoretical number. Since, however, a deficit of hydrogen significantly reduces the selectivity for methanol, a stoichiometric number S of slightly above 2 is considered to be the optimum for methanol synthesis.

The synthesis gas to be used for methanol synthesis is typically obtained from natural gas, other streams comprising hydrocarbons and in some cases also by coal gasification or wood gasification. Standard preparation processes for synthesis gas that are named by Ullmann's Encyclopedia of Industrial Chemistry, "Methanol" chapter, 2012 Wiley-VCH Verlag GmbH & Co. KGaA, Weinheim, Germany are the following four processes:

a) Steam reforming, in which a hydrocarbon feed gas, with addition of water vapor and in the absence of oxygen, is endothermically cleaved catalytically to give hydrogen, carbon monoxide and carbon dioxide.
b) Autothermal reforming, in which a hydrocarbon feed gas, in the presence of a nickel catalyst, is partially exothermically oxidized with oxygen to give hydrogen, carbon monoxide and carbon dioxide.
c) The combination of steam reforming and autothermal reforming.
d) Partial oxidation, in which a hydrocarbon feed gas, in the presence of a catalyst, is partially exothermically oxidized with oxygen to give hydrogen, carbon monoxide and carbon dioxide. As a result of the absence of a catalyst, however, partial oxidation has practical drawbacks compared to autothermal reforming.

Steam reforming generally produces a synthesis gas with a stoichiometric number S of about 3. With regard to methanol synthesis, there is thus a distinct excess of hydrogen. Autothermal reforming and partial oxidation, by contrast, form a synthesis gas with a stoichiometric number S of <2. Therefore, particularly the combination of steam reforming and autothermal reforming offers a variant which is widely practiced industrially, which permits adjustment of the stoichiometric number S to an industrially relevant value of >2.

Since the hydrocarbon feed gas is typically not fully converted in synthesis gas production, the synthesis gas generally comprises greater or lesser proportions of unconverted hydrocarbons, for example methane. Moreover, when air is used as oxidizer in synthesis gas production, greater or lesser proportions of inert extraneous gases, for example nitrogen or argon, are also introduced. These are generally not removed separately, but sent to the methanol synthesis together with the values-containing hydrogen, carbon monoxide and carbon dioxide.

Even though reaction equations (1) and (2) are equilibrium equations and methanol synthesis catalyst is present, the equilibrium is not established quantitatively. Therefore, the reaction mixture directly after the methanol synthesis typically contains only about 5% to 15% by weight of methanol and not inconsiderable amounts of unconverted hydrogen, carbon monoxide, carbon dioxide, and extraneous gases such as methane, nitrogen or argon. Moreover, the reaction mixture also comprises by-products, for example dimethyl ether. The prior art describes various processes for workup of the reaction mixture obtained. Central steps are typically the stepwise concentration of the methanol, handling the values-containing gases with maximum efficiency, and the avoidance of accumulation of extraneous gases.

For instance, in the Lurgi MegaMethanol process described in Ullmann's Encyclopedia of Industrial Chemistry, "Methanol" chapter, chapter 5.2.2, 2012 Wiley-VCH Verlag GmbH & Co. KGaA, Weinheim, Germany, synthesis gas is converted under heterogeneous catalysis to methanol in a methanol synthesis reactor and a methanol-enriched crude methanol stream is first condensed out of the reaction mixture obtained. The remaining gas stream comprises unconverted hydrogen inter alia, and is sent to a pressure swing adsorption for recovery thereof. The hydrogen thus recovered is recycled to the methanol synthesis. The gas stream not absorbed in the pressure swing adsorption is finally sent to thermal utilization. The methanol-enriched liquid stream obtained by the abovementioned condensing-out is subsequently expanded for outgassing and the expansion gas is likewise sent to thermal utilization. The further methanol-enriched liquid stream that remains after the outgassing is then subjected to a multistage distillation for the actual methanol recovery. In this case, the offgas stream from the low boiler column is also sent to thermal utilization.

In the Lurgi MegaMethanol process described, although unconverted hydrogen is removed and recycled to the synthesis, all other gases of value, after they have been separated off, are merely sent to a thermal utilization. Thus, the unconverted carbon monoxide and carbon dioxide also remain unutilized for further recovery of methanol. Even though these remain unutilized for further methanol recovery, the volume flows thereof should, however, be taken into account in the design of the plant, for instance in the form of the required apparatus dimensions for handling of the volume flows. Furthermore, the handling of these volume flows does of course also require energy, for instance in the form of heating, compression or pumping energy, without these being utilized for further methanol synthesis. Moreover, the thermal utilization of the gases of value leads to a further increase in carbon dioxide emission. Combustible gases, which also include carbon monoxide, are converted to carbon dioxide; the carbon dioxide itself that is already present is passed through the thermal utilization unchanged.

It was recognized in EP 2,228,358 A1 that the carbon dioxide present in the crude methanol after synthesis thereof from the synthesis gas also constitutes a valuable feedstock for further methanol synthesis. This is especially true of methanol synthesis in which the synthesis gas has been obtained by steam reforming, since there is a distinct excess of hydrogen here on account of a stoichiometric number S of about 3. EP 2,228,358 A1 teaches recycling carbon dioxide-containing streams from methanol synthesis to the reformer without further workup as feed gas stream for recovery of synthesis gas and hence utilizing the carbon dioxide again as carbon source for the methanol synthesis. FIG. 1 in EP 2,228,358 A1 specifically discloses the recycling of the expansion gas "9" from the expansion of the methanol reactor output and of the offgas stream "10" from the low boiler column as additional feed gas stream to the reformer. However, the offgas "18" from the hydrogen recovery is fed to the reformer as fuel gas. EP 2,228,358 A1 additionally teaches also separating off the carbon dioxide present in the flue gas from the reformer as stream "11" by means of a carbon dioxide recovery unit and feeding it to the reformer as feed gas stream and hence for further utilization in the subsequent methanol synthesis.

A particular disadvantage of the process described is that the direct recycling of the expansion gas and of the offgas stream from the low boiler column results in recycling of the inert gases, for instance nitrogen and argon, as well and hence enrichment of these in the process. Even though the offgas stream from the hydrogen recycling is recycled as fuel gas to the reformer and hence a certain discharge of the inert gases is brought about, the amount of cycle gas nevertheless increases and the conversion to methanol based on the amount of cycle gas decreases. Moreover, the reformer, in accordance with the additional amount of gas resulting from the recycling, should also have a correspondingly large design. The carbon dioxide recovery from the flue gas from the reformer additionally requires a gas scrubbing unit of correspondingly large dimensions, including the incorporation thereof for energy purposes into the overall complex.

U.S. Pat. No. 8,829,059 is also concerned with the recovery and reuse of carbon dioxide from methanol synthesis. Specifically, the document teaches a methanol synthesis method in which the reaction mixture from the methanol synthesis reactor is sent to a condenser to condense out water-containing crude methanol, and the remaining gas that has not been condensed out is split into two substreams. One substream is guided here across the permeate side of a carbon dioxide-sensitive membrane unit and then guided onward via the synthesis gas compressor back to the methanol synthesis reactor. The other substream is guided to the retentate side of a hydrogen-sensitive membrane unit in which a hydrogen-enriched stream is produced on the permeate side for reuse in methanol synthesis. The hydrogen-depleted stream on the retentate side is then guided to the retentate side of the carbon dioxide-sensitive membrane unit already mentioned, in order to increase the carbon dioxide content on the permeate side there and hence to return further carbon dioxide to the methanol synthesis. The process described is shown in a block diagram in FIG. 3 of U.S. Pat. No. 8,829,059.

The use of membrane units in plants of the size of an industrial methanol synthesis plant is relatively costly and inconvenient since correspondingly large membrane areas are required for the handling of the large gas streams. This is particularly true when a high degree of separation is to be achieved. Conversely, however, in the case of a low degree of separation, a portion of the hydrogen and carbon dioxide would remain on the retentate side in each case and would be discharged unutilized from the methanol synthesis process. In addition, there is the risk that the membranes will lose permeability with time as a result of deposits composed of various impurities and/or by-products from the methanol synthesis and have to be changed or cleaned in a complex manner from time to time. Moreover, U.S. Pat. No. 8,829,059 is silent as to the further workup of the water- and methanol-containing stream condensed out in the condenser, which typically still comprises considerable amounts of carbon dioxide dissolved in methanol and water.

S. Reddy et al. in Energy Procedia 63 (2014) 1407-1414 likewise suggests utilizing carbon dioxide from synthesis gas production or from carbon dioxide-containing streams from methanol synthesis for further methanol synthesis. Specifically, the publication teaches absorbing the carbon dioxide from the flue gas from the synthesis gas reformer in an aminic solvent by means of an "Econamine FG Plus$^{SM}$" gas scrubbing unit, then releasing it again as a carbon dioxide stream and feeding this carbon dioxide stream either together with the feed gas stream to the reformer for production of the synthesis gas or feeding it directly straight to the synthesis gas. Moreover, the publication teaches returning what are called purge gases and offgases from the workup of the methanol stream directly to the compression stage upstream of the methanol synthesis reactor and/or feeding them to the reformer as fuel gas. In both cases, the carbon dioxide present therein is fed back to the methanol synthesis. The measures described are said to enable an increase in methanol capacity of about 20%.

In the case of this process too, the direct recycling of purge gases and offgases to the methanol synthesis reactor is disadvantageous since this results in accumulation of inert gases, for instance nitrogen and argon, but also methane or by-products such as dimethyl ether, in the synthesis circuit. In the variant in which the gas streams mentioned are fed to the fuel gas to the reformer, accumulation of inert gases and by-products is counteracted, but the additional amount of gas means that the reformer has to have a correspondingly large design. The carbon dioxide recovery from the flue gas from the reformer additionally requires a gas scrubbing unit of correspondingly large dimensions, including the incorporation thereof for energy purposes into the overall complex.

It was an object of the present invention to find a process for preparing methanol from synthesis gas, which has the abovementioned disadvantages only to a minor degree, if at all, and reacts the carbon monoxide and carbon dioxide present in the synthesis gas virtually completely with hydrogen to give methanol and hence, based on the synthesis gas, has carbon dioxide emission-free operation. The process of the invention is additionally to be easily performable and is to largely use the apparatuses and interconnections in established methanol synthesis processes that are customary in the industry. The process of the invention is thus also to enable easy retrofitting of existing methanol synthesis processes. Technical interventions, modifications or supplementations in the synthesis gas production should be avoided as far as possible for the sake of simplicity.

Figure 1:
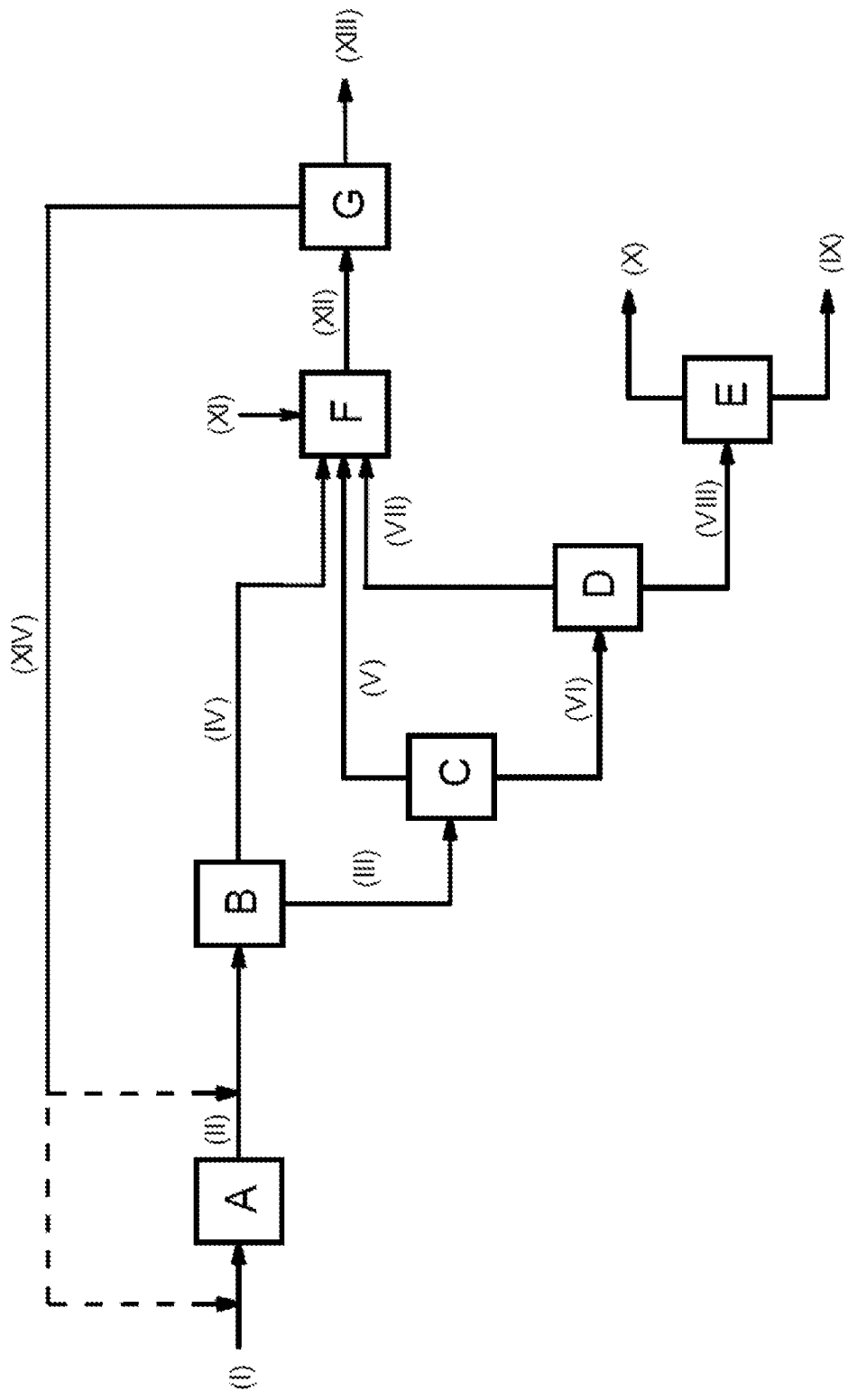
FIG. 1 shows a block diagram of a general embodiment of the process of the invention.

A process for preparing methanol has been found, by
(a) producing a synthesis gas (II) comprising carbon monoxide, carbon dioxide and hydrogen from a carbonaceous feedstock (I) in a synthesis gas production unit (A),
(b) feeding the synthesis gas (II) from stage (a) to a methanol synthesis unit (B) and converting it at a temperature of 150 to 300° C. and a pressure of 5 to 10 MPa abs in the presence of a methanol synthesis catalyst to a reaction mixture containing methanol, water, carbon monoxide, carbon dioxide, hydrogen, dimethyl ether and methane, condensing a methanol- and water-enriched crude methanol stream (III) out of said reaction mixture, and conducting the crude methanol stream (III) and a gaseous stream (IV) comprising carbon monoxide, carbon dioxide, hydrogen and methane out of the methanol synthesis unit (B),
(c) expanding the crude methanol stream (III) from stage (b) in an expansion unit (C) to a pressure of 0.1 to 2 MPa abs, and obtaining an expansion gas (V) comprising carbon dioxide and methane and a degassed crude methanol stream (VI) enriched with methanol and water,
(d) separating a carbon dioxide- and dimethyl ether-comprising low boiler stream (VII) by distillation from the degassed crude methanol stream (VI) from stage (c) in a distillation apparatus (D), and obtaining a methanol- and water-enriched bottom stream (VIII), and
(e) separating a water-containing high boiler stream (IX) from the bottom stream (VIII) from stage (d) in a further distillation apparatus (E), and obtaining methanol by distillation as stream (X), and which comprises
(f) feeding the carbon monoxide, carbon dioxide, dimethyl ether and methane components of value in streams (IV) and in at least one of the two streams (V) and (VII) to a combustion unit (F) and combusting them therein with supply of an oxygenous gas (XI) having an oxygen content of 30% to 100% by volume, forming carbon dioxide-containing flue gas (XII),
(g) separating a carbon dioxide-enriched stream (XIV) from the carbon dioxide-containing flue gas (XII) from stage (f) in a carbon dioxide recovery unit (G) to form an offgas stream (XIII), and
(h) recycling the carbon dioxide-enriched stream (XIV) separated off in the carbon dioxide recovery unit (G) from stage (g) to the synthesis gas production unit (A) of stage (a) and/or to the methanol synthesis unit (B) of stage (b).

The process of the invention is based on the continuously operated methanol synthesis by the low-pressure process known to the person skilled in the art, in which synthesis gas is converted at a pressure of 5 to 10 MPa abs in the presence of a methanol synthesis catalyst to a methanol-containing reaction mixture and subsequently worked up stepwise for isolation of the methanol. The stepwise workup separates off various streams that still comprise components off value or unconverted feedstocks or by-products, for example carbon monoxide, carbon dioxide, dimethyl ether, methane or further by-products. The core of the invention is the physical reuse of the carbon in these components of value for further synthesis of methanol with simultaneous avoidance of carbon dioxide emission. The process of the invention is elucidated in detail hereinafter.

FIG. 1 shows the block diagram of a general embodiment of the process of the invention, in which all three streams (IV), (V) and (VII) are guided to combustion unit (F). The labels therein have the following meanings:
(A) synthesis gas production unit
(B) methanol synthesis unit
(C) expansion unit
(D) distillation apparatus
(E) distillation apparatus
(F) combustion unit
(G) carbon dioxide recovery unit
(I) carbonaceous feedstock
(II) synthesis gas
(III) crude methanol stream
(IV) gaseous stream comprising carbon monoxide, carbon dioxide, hydrogen and methane
(V) expansion gas comprising carbon dioxide and methane
(VI) degassed crude methanol stream
(VII) low boiler stream from distillation apparatus (D)
(VIII) bottom stream from distillation apparatus (D)
(IX) high boiler stream from distillation apparatus (E)
(X) methanol
(XI) oxygenous gas
(XII) flue gas
(XIII) offgas stream from carbon dioxide recovery unit (G)
(XIV) carbon dioxide-enriched stream from carbon dioxide recovery unit (G)

The dotted lines in stream (XIV) indicate that stream (XIV), according to the invention, can either be recycled to the synthesis gas production unit (A) of stage (a) or to the methanol synthesis unit (B) of stage (b), or else split up and sent to both units (A) and (B).

Synthesis gas-producing feedstocks used in the process of the invention may be a wide variety of different carbonaceous feedstocks, irrespective of whether these are in solid, liquid or gaseous form, and irrespective of their chemical nature. For example, synthesis gas can be produced using either coal or hydrocarbons and carbon- and hydrogen-comprising compounds. Preferred carbonaceous feedstocks include natural gas, biogas, coal, wood, plastics, mineral oil, bionaphtha or hydrocarbonaceous streams from mineral oil or natural gas processing, from chemical production methods, from renewable raw materials or from plastics recycling. In the case of coal or wood, synthesis gas is produced, for example, by a gasification process, also called coal gasification or wood gasification. Suitable feedstocks from mineral oil or natural gas processing are, for example, naphtha, LPG, gasoline, heavy oil or vacuum residue. Hydrocarbonaceous streams from chemical production processes are understood to mean, for example, hydrocarbonaceous streams that are obtained as by-products and, rather than a purely thermal utilization, can also be used as feedstock for production of synthesis gas.

Particular preference is given to the use of methane-containing streams and very particular preference to that of natural gas or biogas. In this case it is possible and even advantageous to likewise feed carbon dioxide present in the natural gas and in the biogas in particular to the synthesis gas production unit (A).

In the process of the invention, a synthesis gas (II) comprising carbon monoxide, carbon dioxide and hydrogen is first produced from the carbonaceous feedstock (I) in what is called a synthesis gas production unit (A). Natural gas (I) used in the process of the invention may in principle, for example, be any natural gases suitable for the production of synthesis gas as raw material for methanol synthesis. Natural gas typically comprises 75% to 100% by volume of methane. Accompanying substances alongside methane include in particular the higher hydrocarbons ethane, propane, butane, but also ethene. It is likewise possible in principle, in the process of the invention, to use any biogas suitable for the production of synthesis gas as raw material for methanol synthesis. Biogas typically comprises 40% to 75% by volume of methane and, as accompanying substances, essentially carbon dioxide, water, nitrogen and oxygen.

Typically, the synthesis gas (II) is produced by production methods typically used on the industrial scale, although the nature of the carbonaceous feedstock (I) does of course also play a role here. In the case of methane-containing feedstocks, for instance the case of natural gas or biogas, the synthesis gas (II) is produced in stage (a) preferably by steam reforming, by autothermal reforming, by a combination of steam reforming and autothermal reforming, or by partial oxidation.

A particular advantage of the partial oxidation is that there is no need to supply the synthesis gas production unit with a separate fuel gas, and hence no formation of a carbon dioxide-containing flue gas either. In the partial oxidation, the energy required for synthesis gas production is obtained directly by partial oxidation from the methane-containing feedstock, and the carbon dioxide and carbon monoxide combustion gases formed are likewise used in the methanol synthesis. Therefore, preference is given to the partial oxidation of methane-containing streams, for example natural gas or biogas in the process of the invention.

The typically used interconnections, apparatuses, process parameters, auxiliaries and the workup of the crude synthesis gas obtained are well known to the person skilled in the art and are described extensively in the prior art.

The synthesis gas (II) produced comprises carbon monoxide, carbon dioxide and hydrogen, where the collective concentration thereof is typically 50% to 100% by volume, preferably 80% by volume and more preferably 90% by volume. Possible accompanying substances include, in particular, unconverted constituents of the carbonaceous feedstock used and by-products from the conversion thereof, for example nitrogen, argon, water or methane. Typically, the synthesis gas (II) comprises, as well as carbon monoxide, carbon dioxide and hydrogen, as a result of the preparation, also methane, and also nitrogen and argon, which has been introduced, for example, by the use of air in the synthesis gas production.

According to the manner of production of the synthesis gas (II), it comprises different amounts of carbon monoxide, carbon dioxide and hydrogen. The parameter for specification of the synthesis gas which is relevant and customary for the methanol synthesis is the stoichiometric number S which has already been mentioned above and is defined as $$S = \frac{n(H_2) - n(CO_2)}{n(CO) + n(CO_2)} \qquad (3)$$

where n in each case represents the respective molar amounts. The synthesis gases (II) that are produced in stage (a) and are to be used in stage (b) may vary within a wide range in terms of their stoichiometric number S. In general, in the methanol synthesis unit (B), however, a synthesis gas (II) having a stoichiometric number S in the range from 1 to 5, preferably 1.3, more preferably 1.5 and most preferably 2, and preferably 4, more preferably 3 and most preferably 2.5, is established.

The conversion of the synthesis gas (II) is effected in what is called a methanol synthesis unit (B) at a temperature of 150 to 300° C. and a pressure of 5 to 10 MPa abs in the presence of a methanol synthesis catalyst. For this purpose, the synthesis gas (II) is typically compressed to the desired pressure by means of a compressor and converted in a reactor under the conditions specified.

The conversion is preferably effected at a temperature of 170° C. and more preferably at 190° C., and preferably at 280° C. and more preferably at 260° C. With regard to the pressure, the conversion is effected preferably at 6 MPa abs and preferably at 9 MPa abs.

Reactors used may in principle be any reactors that are suitable for the exothermic conversion of synthesis gas to methanol under the process conditions specified. Reactors for synthesis of methanol from synthesis gas are common knowledge to the person skilled in the art. Examples of these include the adiabatic and quasi-isothermal reactors, variobar reactors and what are called double-wall superconverters that are mentioned in Ullmann's Encyclopedia of Industrial Chemistry, "Methanol" chapter, Section 5.2.1 "Reactor Design", 2012 Wiley-VCH Verlag GmbH & Co. KGaA, Weinheim, Germany.

Methanol synthesis catalysts that may be used in the process of the invention are virtually any catalysts suitable for the conversion of synthesis gas to methanol under the process conditions mentioned. Corresponding methanol synthesis catalysts are common knowledge to those skilled in the art. Examples of these include the copper- and zinc-containing heterogeneous catalysts that are mentioned in Ullmann's Encyclopedia of Industrial Chemistry, "Methanol" chapter, Section 4.2 "Catalysts", 2012 Wiley-VCH Verlag GmbH & Co. KGaA, Weinheim, Germany. In general, these also comprise further elements, for example aluminum, rare earths or chromium.

The conversion of the synthesis gas (II) comprising carbon monoxide, carbon dioxide and hydrogen forms methanol and water in accordance with reaction equations (1) and (2)

$$CO + 2H_2 \rightleftharpoons CH_3OH \quad (1)$$

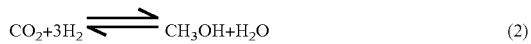
$$CO_2 + 3H_2 \rightleftharpoons CH_3OH + H_2O \quad (2)$$

A typical by-product formed is dimethyl ether. In addition, full hydrogenation of carbon monoxide or carbon dioxide also gives rise to methane as a further by-product. The reaction mixture produced in the reactor thus comprises methanol, water, dimethyl ether, carbon monoxide, carbon dioxide, hydrogen and methane. Additionally formed under the reaction conditions mentioned, however, are typically also further by-products, for example methyl formate, acetic acid, higher alcohols having carbon numbers of 2, esters and ethers having carbon numbers of >2, and also paraffins.

For separation of the complex reaction mixture, a methanol- and water-enriched crude methanol stream (III) is first condensed out. For this purpose, the reaction mixture produced in the reactor is typically fed to a condenser. Condensers used may be the apparatuses known to the person skilled in the art that are suitable for obtaining a methanol- and water-enriched condensate by controlled cooling under the present conditions. In general, the reaction mixture is cooled down to a temperature below the dew point of methanol. In accordance with the solubilities and vapor pressures of the components present in the reaction mixture, the methanol- and water-enriched crude methanol stream (III) still comprises gases dissolved therein, for example hydrogen, carbon monoxide, carbon dioxide, dimethyl ether, methane, and higher-boiling components than methanol. The crude methanol stream (III) condensed out is then discharged from the methanol synthesis unit (B) for further workup and guided to stage (c).

The uncondensed gas stream especially comprises the unconverted carbon monoxide, carbon dioxide and hydrogen feedstocks, and methane. In order to obtain a high partial pressure of the synthesis gas components hydrogen, carbon monoxide and carbon dioxide, a portion of the uncondensed gas stream is typically discharged. If required, this discharged gas stream is sent to a removal of hydrogen in order to increase the partial pressure of hydrogen in the reactor. A higher partial pressure of hydrogen in the reactor reduces the formation of secondary components and especially also suppresses the Fischer-Tropsch reaction. The predominant portion of the uncondensed gas stream is recycled into the methanol synthesis unit as cycle gas and guided over the methanol synthesis catalyst in order to achieve maximum exploitation of the synthesis gas and hence high yields of methanol.

Accordingly, the methanol synthesis unit (B) in stage (b) advantageously comprises a compressor for compression of the synthesis gas (II), a reactor for conversion of the synthesis gas (II), a condenser for condensing out the crude methanol stream (III), and a conduit for recycling of uncondensed gas to the reactor.

Depending on the composition of the synthesis gas (II) supplied, it is thus already possible to establish a stoichiometric number S of >2 at the reactor inlet. Preferably, in the process of the invention, by means of recycled synthesis cycle gas and optionally also by means of the additional recycling of hydrogen from the further workup of the discharged synthesis cycle gas and the supply of fresh hydrogen to the methanol synthesis unit (B), a stoichiometric number S at the reactor inlet of preferably 2.5 and more preferably of 2.8, and preferably 4 and more preferably of 3.8, is established.

The uncondensed gas stream that has not been recycled as synthesis cycle gas is discharged from the methanol synthesis unit (B) as gaseous stream (IV) and guided to stage (f) of the invention. The amount of gas stream (IV) to be discharged is found from the mass balance of the streams supplied to and removed from the methanol synthesis unit (B).

In stage (c) of the process of the invention, the crude methanol stream (III) that has been condensed out in stage (b) and discharged from the methanol synthesis unit (B) is expanded in an expansion unit (C) to a pressure of 0.1 to 2 MPa abs, and an expansion gas (V) comprising carbon dioxide and methane and a degassed crude methanol stream (VI) enriched with methanol and water are obtained. The expansion is typically effected in an apparatus in which gas phase and liquid phase can be efficiently separated from one another. Typically, the apparatus is a liquid separator. Suitable apparatuses for this purpose are known to those skilled in the art.

The expansion is preferably effected to a pressure of 0.2 MPa abs and more preferably to 0.4 MPa abs, and preferably to 1.5 MPa abs and more preferably to 1 MPa abs. In general, the temperature of the expanded mixture is 0 to 150° C., preferably 10° C. and more preferably 20° C., and preferably 120° C. and more preferably 60° C.

The degassed crude methanol stream (VI) has been further enriched in methanol and water, but also comprises further components in accordance with the solubilities and vapor pressures of the components present in the crude methanol stream (III), for example gases dissolved therein such as hydrogen, carbon monoxide, carbon dioxide, dimethyl ether, methane or higher-boiling components than methanol.

The expansion gas (V) comprising carbon dioxide and methane is preferably guided to stage (f) of the invention. Alternatively, the expansion gas (V) can, however, also be discharged from the methanol synthesis plant and, for example, be utilized thermally or disposed of in some other way. However, preference is given to the utilization thereof within the methanol synthesis plant as feed stream to the combustion unit (F).

In stage (d) of the process of the invention, the degassed crude methanol stream (VI) obtained in stage (c) is separated by distillation in a distillation apparatus (D) into a low boiler stream (VII) comprising carbon dioxide and dimethyl ether, and a bottom stream (VIII) enriched with methanol and water. Useful distillation apparatuses in principle include the apparatuses known to the person skilled in the art for such separation tasks or those to be designed by applying common knowledge in the art. Typically, the distillative separation in step (d) is effected in a single distillation column, although it is of course also possible to operate multiple distillation columns in parallel. As well as the actual column body with internals, the distillation column, as usual, also comprises a top condenser and a reboiler. The column body may have been equipped, for example, with structured packings, random packings or trays. The distillation apparatus (D) may be designed and operated by the common knowledge of the person skilled in the art.

The low boiler stream (VII) separated off by distillation comprises primarily carbon dioxide and dimethyl ether as low boilers that have been separated off and, based on the composition of the degassed crude methanol stream (VI), further low boilers, for example methane, and also, depending on the separation performance and mode of operation of the distillation apparatus, methanol or higher-boiling components than methanol, for example water. The low boiler stream (VII) comprising carbon dioxide and dimethyl ether is likewise preferably guided to stage (f) of the invention. If the expansion gas (V) is sent to the combustion unit (F) and hence reused directly within the methanol synthesis plant, the low boiler stream (VII) can alternatively also be discharged from the methanol synthesis plant and, for example, utilized thermally or disposed of in some other way. However, preference is given to utilization thereof within the methanol synthesis plant as feed stream to the combustion unit (F).

The methanol- and water-enriched bottom stream (VIII) additionally also comprises further components that are higher-boiling than methanol, for example higher-boiling by-products than methanol from the methanol synthesis, for instance acetic acid, higher alcohols, higher esters, higher ethers or paraffins.

To obtain the methanol, finally, in stage (e), a water-containing high boiler stream (IX) is separated from the bottom stream (VIII) obtained in stage (d) in a further distillation apparatus (E) and methanol is obtained by distillation as stream (X). Useful distillation apparatuses for stage (e) in principle include the apparatuses known to the person skilled in the art for such separation tasks or those to be designed by applying common knowledge in the art. In principle, the distillative separation in stage (e) can be effected in a single distillation column. As well as the actual column body with internals, the distillation column, as usual, also comprises a top condenser and a reboiler. The column body may have been equipped, for example, with structured packings, random packings or trays. It is of course also possible to operate multiple distillation columns in parallel or to remove the methanol stepwise in multiple distillation columns. The distillation apparatus (E) may be designed and operated by the common knowledge of the person skilled in the art.

Methanol is typically obtained as top product as stream (X). But it is also possible in principle to obtain methanol as what is called a side stream and to remove low boilers still present as a top stream.

A variant which is attractive in terms of energy is called the two-pressure distillation. In this variant, two distillation columns are connected in series and coupled to one another in terms of energy. The first distillation column is operated under pressure, typically at 0.5 to 1.5 MPa abs, and methanol is removed overhead as low boiler. The first distillation column is operated in such a way that some of the methanol remains in the bottoms, and these are sent to a second distillation column. The second distillation column is operated at a lower pressure, for example atmospheric pressure. The bottom of the second distillation column is coupled in terms of energy to the low boiler stream from the first distillation column, meaning that the amount of heat released on cooling of the low boiler stream from the first distillation column serves to heat up the second distillation column. In the second distillation column too, methanol is removed overhead as low boiler. The high boilers obtained in the bottom of the second distillation column are removed and discharged. The construction and operation of the two-pressure distillation and especially of the two-pressure distillation for obtaining methanol are known to the person skilled in the art.

The high boiler stream (IX) comprises water and also further components that are higher-boiling than methanol, for example higher-boiling by-products than methanol from the methanol synthesis, for instance acetic acid, higher alcohols, higher esters, higher ethers or paraffins. This stream can be sent to a wastewater treatment, for example.

Via stream (X), methanol can be obtained in a high purity of 95% by weight, preferably 98% by weight and more preferably 99% by weight. Accompanying substances include residual amounts of low and high boilers that have not been removed completely by distillation, especially water, and very small amounts of ethanol, esters and ethers.

In the stepwise workup of the reaction mixture to obtain the methanol as stream (X), streams (IV), (V) and (VII) are separated off. However, these still contain components of value, for example carbon monoxide, carbon dioxide, methane and dimethyl ether. The core of the invention is the substantial physical reuse of the carbon in these components of value for further synthesis of methanol with simultaneous avoidance of carbon dioxide emission.

The stages (f) to (h) that are essential to the invention are elucidated in detail hereinafter.

The process of the invention comprises
f) feeding the carbon monoxide, carbon dioxide, dimethyl ether and methane components of value in streams (IV) and in at least one of the two streams (V) and (VII) to a combustion unit (F) and combusting them therein with supply of an oxygenous gas (XI) having an oxygen content of 30% to 100% by volume, forming a carbon dioxide-containing flue gas (XII),
g) separating a carbon dioxide-enriched stream (XIV) from the carbon dioxide-containing flue gas (XII) from stage (f) in a carbon dioxide recovery unit (G) to form an offgas stream (XIII), and
h) recycling the carbon dioxide-enriched stream (XIV) separated off in the carbon dioxide recovery unit (G) from stage (g) to the synthesis gas production unit (A) of stage (a) and/or to the methanol synthesis unit (B) of stage (b).

Preferably, in stage (f), the carbon monoxide, carbon dioxide, dimethyl ether and methane components of value in streams (IV), (V) and (VI) are fed to the combustion unit (F).

Since the methane and dimethyl ether components of value in streams (IV), (V) and (VII), but also other carbon-containing by-products present therein, cannot be used directly in this form as reactants for the methanol synthesis, it is necessary first to convert them chemically to a suitable form. The solution of the invention therefore envisages combusting these in a combustion unit (F) to form a carbon dioxide-containing flue gas. The conversion to carbon dioxide makes it possible also to reuse the components of value methane, dimethyl ether and further carbon-containing by-products as reactant in the methanol synthesis. Therefore, in the process of the invention, streams (IV), (V) and (VII) are first sent to a combustion unit (F). The combustible components of value are burned therein with supply of an oxygenous gas (XI) having an oxygen content of 30% to 100% by volume. The combustion is typically effected in what is called a combustion chamber with formation of carbon dioxide and water. The combustion is typically effected at atmospheric pressure. But it is also possible to conduct the combustion at a lower or higher pressure. For the sake of completeness, a pressure range from 0.05 to 0.5 MPa abs is stated.

Combustion chambers used may in principle be any apparatuses suitable for the highly exothermic oxidation of a corresponding stream comprising carbon monoxide, methane and dimethyl ether with an oxygenous gas having an appropriate oxygen content. Suitable combustion chambers are known to the person skilled in the art or can be designed and operated with the common knowledge of the person skilled in the art. Examples include, for instance, adiabatic combustion chambers or reactors with outcoupling of heat, such as directly fired steam generators, for instance in the form of water-tube boilers or flame-tube or smoke-tube boilers.

A significant advantage of the inventive use of an oxygenous gas (XI) having an oxygen content of 30% to 100% by volume is a much higher content of carbon dioxide in the combustion gas obtained compared to the use of air with only about 21% by volume of oxygen. Correspondingly, in the process of the invention, compared to air as oxidizer, the proportion of unwanted inert gases, for instance nitrogen or argon, is of course also much lower.

Preferably, the combustion unit (F) is supplied with an oxygenous gas (XI) having an oxygen content of ≥50% by volume, more preferably of ≥80% by volume, even more preferably of ≥90% by volume, in particular of ≥95% by volume, and especially pure oxygen. When pure oxygen is used in the combustion, this is also called an oxyfuel process.

Typically ≥90%, preferably ≥95%, more preferably ≥98% and most preferably ≥99% of the carbon in the combustible components is thus converted to carbon dioxide.

A further advantage resulting from the use of an oxygen-rich gas as oxidizer rather than air is also the distinct reduction in thermally formed nitrogen oxides NON. In the case of use of pure oxygen and only a very small content of nitrogen via the streams (IV), (V) and (VII) supplied, the formation of nitrogen oxides NO can even be virtually completely avoided.

Furthermore, combustion processes with oxygen-rich gases as oxidizer are more energy-efficient compared to air owing to the higher combustion temperatures. For example, in the combustion of pure methane, when air is used, a theoretical combustion temperature of about 1800 to 2000° C. is found, whereas the combustion of pure methane with pure oxygen results in a theoretical combustion temperature of about 4000 to 5000° C. In order to counteract a particularly high combustion temperature, for material-related reasons in particular, in the combustion of the invention, a portion of the flue gas is typically recycled into the combustion chamber for temperature control after cooling.

Since, when an oxygenous gas (XI) with a correspondingly high oxygen content is used, the flue gas formed has only a correspondingly small content of nitrogen, or is virtually free of nitrogen, a correspondingly small separation stage is generally also sufficient for separation of the nitrogen from the carbon dioxide.

In order to further increase the content of carbon dioxide in the combustion gas obtained, it is generally advantageous to reduce the water content prior to the discharge from the combustion unit (F). Typically, this is effected by simple condensing-out in a condenser. Condensers used may be the apparatuses known to the person skilled in the art that are suitable for separating water as condensate from a carbon dioxide- and water-containing gas stream by controlled cooling under the present conditions. In general, the combustion gas is cooled down to a temperature below the dew point of water. If water is condensed out, this is discharged from the combustion unit (F) as stream (XV), and the remaining water-depleted combustion gas as carbon dioxide-containing flue gas (XII). Preferably 50% to 100%, more preferably 80% and most preferably 90% of the water present in the combustion gas is condensed out.

Figure 2:
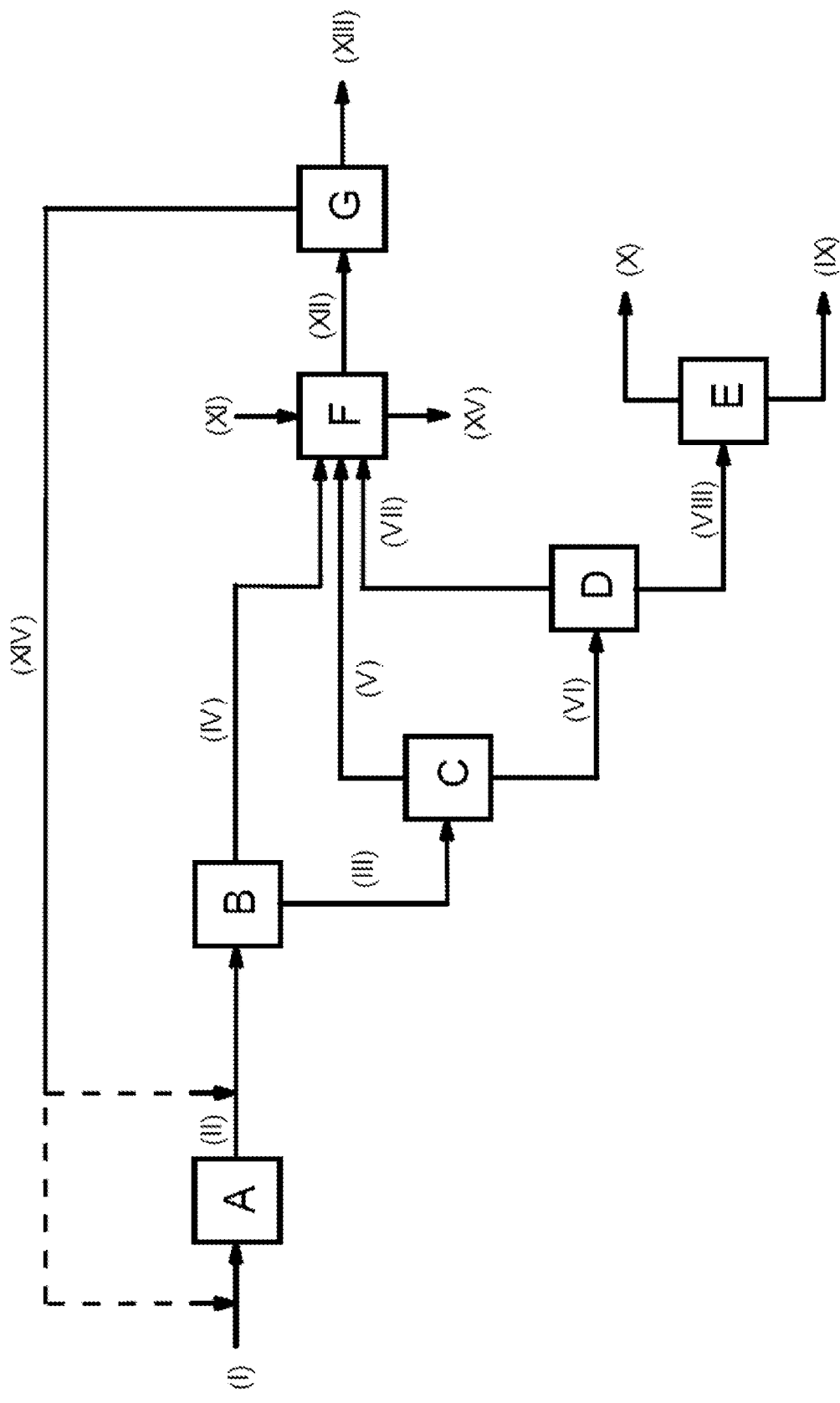
FIG. 2 shows a block diagram of a general embodiment in which water is condensed out of the combustion gas and conducted away as stream (XV).

Preference is thus given to a process in which the combustion unit (F) in stage (f) comprises a combustion chamber and a condenser, water is condensed out of the combustion gas obtained in the combustion chamber in the condenser and conducted out of the combustion unit (F) as stream (XV), and the remaining gaseous stream constitutes the carbon dioxide-containing flue gas (XII). FIG. 2 shows a block diagram of a general embodiment in which water is condensed out of the combustion gas and conducted away as stream (XV).

However, it is also possible, albeit not preferable, to leave the water entirely in the combustion gas and to discharge it from the combustion unit (F) together with the carbon dioxide as carbon dioxide-containing flue gas (XII).

An appraisal illustrates the significant increase in the carbon dioxide content in the flue gas (XII) by the use of pure oxygen compared to air as oxidizer, and by the subsequent removal of the water. For instance, in a theoretical appraisal of the combustion of pure methane to give carbon dioxide and water, in the case of air as oxidizer, a carbon dioxide content in the combustion gas of around 9% by volume, and even after complete combustion of the water, of only 12% by volume is achieved. By contrast, the use of pure oxygen as oxidizer already leads to a carbon dioxide content in the combustion gas of around 33% by volume. By completely condensing out the water, it is even possible to achieve a theoretical carbon dioxide content of 100% by volume. This corresponds to an increase in the carbon dioxide content with use of pure oxygen as opposed to air by a factor of 3.7 (9% by volume vs. 33% by volume) without removal of the water, and even by a factor of 8.3 (12% by volume vs. 100% by volume) with removal of the water. Depending on the actual composition of the gas supplied to the combustion unit (F), somewhat different factors are of course found. Nevertheless, the use of pure oxygen as oxidizer leads in each case to a significantly higher carbon dioxide content in the combustion gas and, especially after the condensing-out of water, in the discharged flue gas (XII) as well.

Particularly as a result of the use of pure oxygen as oxidizer, the flue gas (XII) has a distinctly higher content of the carbon dioxide component of value. In other words, the use of pure oxygen, given the same absolute amount of carbon dioxide, results in formation of significantly less flue gas. Thus, in the process of the invention, the size of the combustion unit (F) and especially of the combustion chamber and the condenser and downstream apparatuses and conduits may have correspondingly smaller dimensions.

As well as carbon dioxide as component of value, the flue gas (XII) obtained generally still comprises various inert gases that have been fed to the combustion unit (F) via streams (IV), (V) and (VII) and/or the oxygenous gas (XI), such as nitrogen or argon. Since the combustion is typically incomplete with regard to the oxygen supplied as well, the flue gas (XII) generally also comprises unconverted oxygen, typically in the range from 2% to 20% by volume. According to whether and to what extent water has been condensed out of the combustion gas, the flue gas (XII) also still comprises the water formed in the combustion and the fraction uncondensed after condensing out the water. In general, the flue gas (XII) discharged from the combustion unit (F) has a carbon dioxide content of 25% to 90% by volume, preferably 50% by volume, more preferably 60% by volume and most preferably 70% by volume, and preferably 85% by volume and more preferably 80% by volume.

A carbon dioxide-enriched stream (XIV) is then separated in stage (g) from the carbon dioxide-containing flue gas (XII) formed in stage (f) in a carbon dioxide recovery unit (G) to form an offgas stream (XIII). Carbon dioxide recovery units (G) used may in principle be all apparatuses and processes suitable for the separation and concentration of carbon dioxide from carbon dioxide-containing gas streams that comprise, as well as carbon dioxide, also inert gases, for instance nitrogen and argon, and possibly water as further components. Corresponding apparatuses and processes are known to those skilled in the art. A general overview of possible apparatuses and processes can be found, for example, in Ullmann's Encyclopedia of Industrial Chemistry, "Carbon Dioxide" chapter, Section 13.3 "CCS-related Separation Technologies", 2014 Wiley-VCH Verlag GmbH & Co. KGaA, Weinheim, Germany. Examples include what are called the gas scrubbing processes in which the carbon dioxide is physically or chemically absorbed in what is called a gas scrubbing solvent and subsequently desorbed again, and membrane processes in which the carbon dioxide is separated off by means of a carbon dioxide-sensitive membrane.

In the case of physical absorption, the carbon dioxide is absorbed in an absorber under elevated pressure in a suitable solvent, for instance methanol, N-methylpyrrolidone or polyethylene glycol dimethyl ether, and subsequently desorbed again under expansion in a desorber. The carbon dioxide-depleted solvent is typically recycled back to the absorber. The physical absorption typically requires pressures in the range from about 2 to 5 MPa abs. However, since the carbon dioxide-containing flue gas (XII) is typically only at a pressure of 0.1 to 0.3 MPa abs, it would first have to be compressed with expenditure of energy.

In the process of the invention, preference is therefore given to chemical absorption in a solvent that chemically binds carbon dioxide. Chemical absorption generally does not require higher pressures, and so there is no need first to compress the carbon dioxide-containing flue gas (XII) in an energy-intensive manner. Chemically active solvents that are mentioned are basic solvents in particular. In chemical absorption, in the carbon dioxide recovery unit (G) in stage (g), carbon dioxide is absorbed from the carbon dioxide-containing flue gas (XII) in an absorber in a basic solvent to form the offgas stream (XIII) and subsequently desorbed again at higher temperature in a desorber. The carbon dioxide-depleted solvent is typically recycled back to the absorber.

Preference is therefore given to a process in which, in the carbon dioxide recovery unit (G) in stage (g), carbon dioxide is absorbed from the carbon dioxide-containing flue gas (XII) in an absorber in a basic solvent to form the offgas stream (XIII), a carbon dioxide-enriched stream (XIV) is released from the carbon dioxide-laden solvent in a desorber, and the carbon dioxide-depleted solvent is returned to the absorber.

The basic solvents are typically aqueous solutions of basic inorganic or organic substances. Basic inorganic substances include, for instance, salts of hydrogencarbonate, and basic organic substances include organic amines. Typically, the water content of the aqueous solutions is 20% to 80% by weight, preferably 40% by weight and more preferably 50% by weight.

The basic solvent used in the process of the invention is more preferably an aqueous solution of an organic amine. The amines may be linear or cyclic, unbranched or branched compounds. Suitable amines are mentioned, for example, in US 2008/236,390, US 2010/192,770 or US 2011/094,381. The organic amines preferably have a molar mass of 50 to 500 g/mol. Particular preference is given to the use of monoethanolamine, piperazine, 2-amino-2-methyl-1-propanol, triethylenediamine, N-methyldiethanolamine, tert-butylaminoethoxyethanol, very particular preference to that of N-methyldiethanolamine.

Typically, in the chemical absorption, the carbon dioxide-containing flue gas (XII) is contacted with the basic solvent in the absorber at a temperature of 10 to 100° C., preferably 20° C., and preferably 60° C. and more preferably 40° C. Absorbers used may in principle be any apparatuses suitable for absorption of carbon dioxide from a carbon dioxide-containing flue gas stream. Suitable apparatuses for the purpose are known to the person skilled in the art and can be designed with common knowledge in the art. Typically, absorption is accomplished using what are called absorption columns. For better heat and mass transfer, these advantageously comprise structured packings or trays. On contact with the basic solvent, the carbon dioxide is chemically bound therein. The components not absorbed in the basic solvent are conducted out of the absorption column as offgas stream (XIII) as what is called the purge stream. The carbon dioxide-laden solvent is drawn off at the bottom of the absorber, fed to the absorber and stripped with steam therein in order to release the carbon dioxide again. Advantageously, the desorber is preferably operated at a temperature of 40 to 110° C. higher than the absorber. Suitable apparatuses for the purpose are likewise known to the person skilled in the art and can be designed with common knowledge in the art. Typically, desorption is accomplished using what are called desorption columns. For better heat and mass transfer, these also advantageously comprise structured packings or trays. Water is first advantageously condensed out of the desorption stream obtained at the top of the desorber. The water condensed out can then, for example, be recycled back into the carbon dioxide recovery process. The solvent that has been depleted of carbon dioxide and water is then recycled to the absorber.

Both absorber and desorber are typically operated at 0.1 to 0.3 MPa abs; the exact pressures are generally guided by the downstream process steps and can be determined easily by the person skilled in the art. Alternatively, the absorption can also be operated at higher pressures.

The carbon dioxide absorption capacity of the solvent in that case is higher than under conditions close to ambient pressure. As a result, the regeneration in the desorber is also more energy-efficient. However, in this variant, the carbon dioxide-containing flue gas (XII) would have to be compressed, which has an adverse effect on the overall energy balance. Therefore, absorber and desorber are preferably operated at 0.1 to 0.3 MPa abs.

Since the desorption is typically effected at higher temperature than the absorption, the carbon dioxide-laden solvent withdrawn from the absorber should be heated, and the carbon dioxide- and water-depleted solvent withdrawn from the desorber should be cooled for reuse thereof in the absorber. It is therefore particularly advantageous for the energy efficiency of the carbon dioxide recovery to use what is called a crossflow heat exchanger, in which the warmer solvent from the desorber heats up the colder solvent from the absorber. The use of further solvent heat exchangers can further increase the energy efficiency of the process. The exact setting of the temperature of the carbon dioxide-depleted solvent for use thereof in the absorber can then be effected, for example, by means of an air or water cooler.

In addition, it is possible to further increase the energy efficiency of the carbon dioxide recovery by further thermal integration measures, for example by the use of a liquid cooler in the lower absorber region. Solvent losses can also be reduced by further measures. For example, it is possible, and advantageous in the case of solvents having a non-negligible vapor pressure, to guide the gas stream through a scrubbing bed in the upper absorber region and to cool the liquid phase via direct cooling with a circulation cooler.

In order to compensate for losses of solvent, which generally cannot be entirely avoided in spite of various countermeasures, solvent or individual solvent components are typically supplied as what is called a makeup stream. It is thus possible to keep the levels in the two columns constant over time. Typically, the supply is effected at the top of the absorber.

The carbon dioxide recovery unit (G) selectively removes the carbon dioxide from the flue gas (XII) and recovers it in the form of a carbon dioxide-enriched stream (XIV) for further use in the methanol synthesis. Typically, the carbon dioxide-enriched stream (XIV) comprises carbon dioxide at a level of 80% to 100% by volume on an anhydrous basis, preferably 97% by volume on anhydrous basis, and small amounts of extraneous gases, for example nitrogen, oxygen or argon, but these are typically below 0.3% by volume on an anhydrous basis. In addition, the carbon dioxide-enriched stream (XIII) typically also comprises water, which, however, has already been excluded in the abovementioned percentages by volume.

The carbon dioxide recovery processes mentioned are notable for a relatively high carbon dioxide recovery rate, the carbon dioxide recovery rate being understood to mean the ratio between the amount of carbon dioxide which is fed to the carbon dioxide recovery unit (G) via the carbon dioxide-containing flue gas (XII) and the amount of carbon dioxide which is conducted out of the carbon dioxide recovery unit (G) via the carbon dioxide-enriched stream (XIV). The processes mentioned can easily achieve carbon dioxide recovery rates of 90% to almost 100%. The carbon dioxide recovery rate is preferably 95%, more preferably 98% and most preferably 99%, and preferably 99.9%.

The offgas stream (XIII) comprises the components of the flue gas (XII) that have not been separated off via the carbon dioxide-enriched stream (XIV), especially inert gases, for instance nitrogen or argon, but also oxygen and water that has not been separated off in the carbon dioxide recovery unit (G). By means of the offgas stream (XIII), in particular, inert gases are thus selectively discharged from the methanol synthesis process and hence unwanted accumulation is counteracted. The offgas stream (XIII) thus functions not just as offgas stream for the carbon dioxide recovery unit (G) but at the same time also assumes the important function of what is called the purge stream for discharge of inert gases from the methanol synthesis.

The carbon dioxide-enriched stream (XIV) separated off in the carbon dioxide recovery unit (G) is subsequently recycled to the synthesis gas production unit (A) of stage (a) and/or to the methanol synthesis unit (B) of stage (b). The recycling of the invention can thus be effected either to the synthesis gas production unit (A) of stage (a) or to the methanol synthesis unit (B) of stage (b), or split between the two.

In the case of the recycling of the carbon dioxide to the synthesis gas production unit (A), this can be supplied, for example, to the carbonaceous feedstock (I) and then used together therewith for production of the synthesis gas (II). According to the nature of the synthesis gas production, the carbon dioxide passes through the synthesis gas production unit (A) in unchanged form as carbon dioxide or is converted to a greater or lesser degree by reaction with the hydrogen formed or by reaction with water added or formed to carbon monoxide. In the case of recycling of the carbon dioxide to the methanol synthesis unit (B), this can be supplied, for example, to the synthesis gas (II) and then used together therewith for synthesis of methanol. For the sake of completeness, it should be stated that, in the case of splitting of the recycling of the carbon dioxide, the split ratio can of course vary over the entire range between 0% and 100%. In all the cases mentioned, however, the carbon from the carbon dioxide can in each case be physically utilized for further synthesis of methanol.

Even though stream (XIV) can be recycled without difficulty to the synthesis gas production unit (A) of stage (a), for the sake of simplicity, it is advantageous and preferable to recycle stream (XIV) from stage (g) to the methanol synthesis unit (B) of stage (b).

Since stream (XIV) is typically at a pressure of 0.1 to 0.3 MPa abs, but the methanol synthesis is effected at a pressure of 5 to 10 MPa abs, it is advantageous in the case of recycling of stream (XIV) to the methanol synthesis unit (B) to feed stream (XIV) to the synthesis gas compressor and then to feed it into the reactor together with the compressed synthesis gas.

Since the carbon dioxide-enriched stream (XIV) generally still comprises small amounts of oxygen, typically in the order of magnitude of a few ppm by volume to a few hundred ppm by volume, and oxygen has an adverse effect on the methanol synthesis with regard to catalyst service life and performance, it is advantageous to reduce the oxygen content of stream (XIV). In principle, it is possible for this purpose to use various processes capable of removing small amounts of oxygen from a carbon dioxide-containing stream. A simple process for this purpose is the catalytic hydrogenation of the oxygen to water. Examples of suitable catalysts for this purpose include copper- or precious metal-containing fixed bed catalysts. Suitable processes and the design and operation thereof are known to those skilled in the art. It is thus advantageous to catalytically hydrogenate stream (XIV) prior to recycling thereof to the synthesis gas production unit (A) or to the methanol synthesis unit (B) to deplete the oxygen. By the hydrogenation mentioned, it is easily possible to reduce the oxygen content to values <1 ppm by volume.

As well as the carbon dioxide recycled via stream (XIV), it is also possible in the process of the invention also to feed carbon monoxide from other sources to the synthesis gas production unit (A) of stage (a) and/or to the methanol synthesis unit (B) of stage (b). Carbon dioxide from "other sources" includes, for example, carbon dioxide from various flue gases, for example from the flue gas from synthesis gas production, from power plants or from other combustion processes, where the carbon dioxide is preferably isolated from the flue gases beforehand, for example by means of a carbon dioxide recovery unit.

The process of the invention for preparing methanol is conducted continuously.

It is thus possible by the process steps of the invention to reuse the carbon in the components of value specifically for the further synthesis of methanol, i.e. to produce further product of value, and at the same time to avoid emission of carbon dioxide from the methanol synthesis.

The methanol synthesis can thus be operated free of carbon dioxide emissions.

As already mentioned at the outset, a stoichiometric number S $$S = \frac{n(H_2) - n(CO_2)}{n(CO) + n(CO_2)} \qquad (3)$$

of 2 corresponds to the theoretical stoichiometry of the methanol synthesis from carbon monoxide, carbon dioxide and hydrogen. Depending on the source of the synthesis gas (II), it may already have a stoichiometric number S of >2, for instance in the case of synthesis gas from the steam reforming of methane-containing gas with a theoretical value of 3. With regard to reduced formation of unwanted secondary components, however, a stoichiometric number at the reactor inlet of well above 2, and more preferably of 2.8 to 3.8, is desirable. In order to attain these values, a distinct excess of hydrogen is required. However, it should be noted that hydrogen is conducted out of the methanol synthesis unit (B), for example via stream (IV). When a hydrogen-rich synthesis gas (II), for instance from steam reforming, is used, the loss of hydrogen can usually be tolerated. By contrast, when a less hydrogen-rich synthesis gas (II) is used, it is often advantageous not to combust the hydrogen from stream (IV) to give water in the combustion unit (F), but to separate it off and recycle it to the methanol synthesis.

Figure 3:
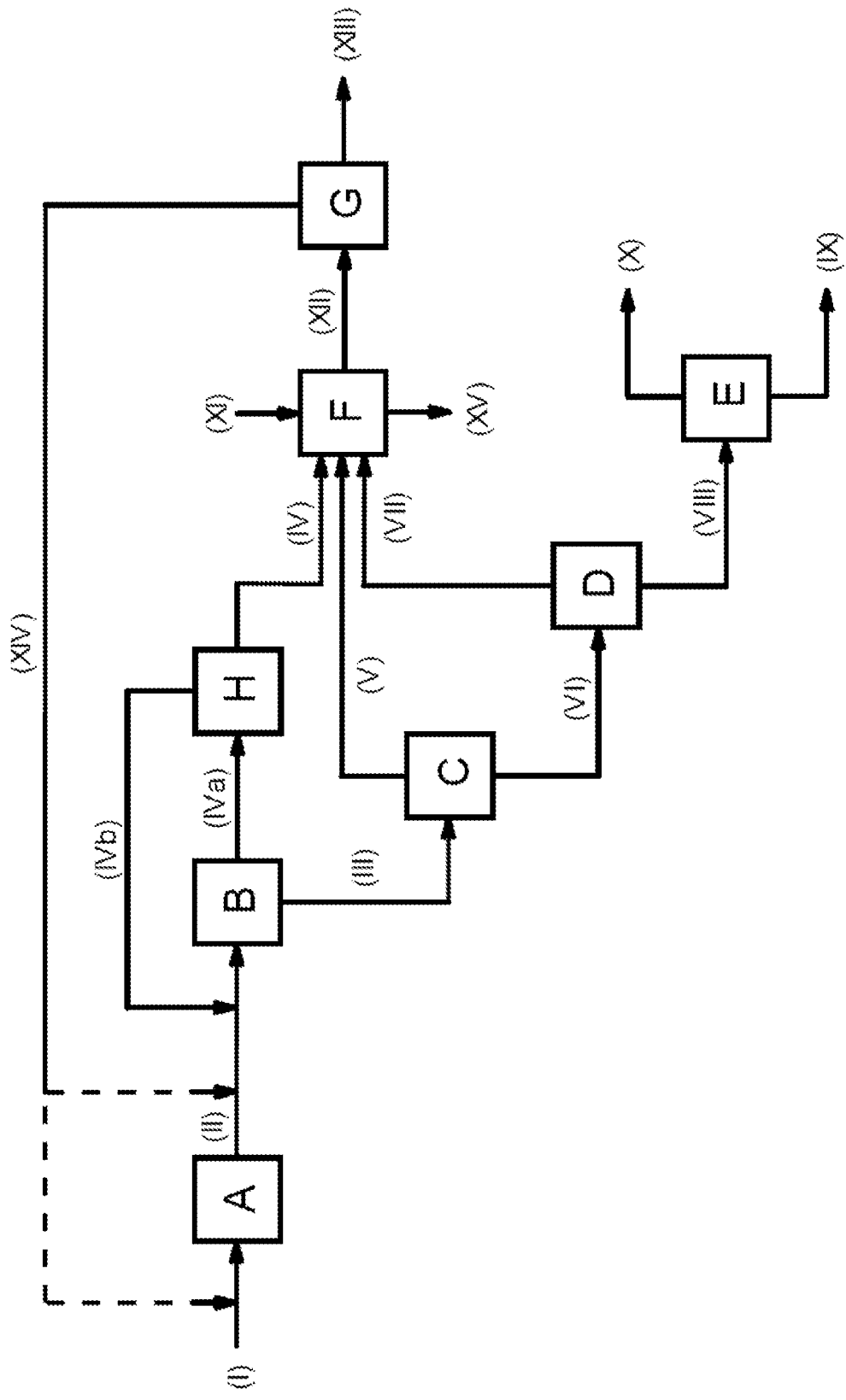
FIG. 3 shows a block diagram of a general embodiment in which hydrogen is separated off in hydrogen recovery unit (H) and recycled.

In a preferred variant of the process of the invention, therefore, before stream (IV) is fed to the combustion unit (F), hydrogen is separated off in a hydrogen recovery unit (H) and recycled to the methanol synthesis unit (B) of stage (b). FIG. 3 shows a block diagram of a general embodiment in which hydrogen is separated off in a hydrogen recovery unit (H) and recycled. In general, it is advantageous to feed the hydrogen separated off to the synthesis gas compressor in the methanol synthesis unit (B) and then to feed it into the reactor together with the compressed synthesis gas.

In principle, the hydrogen can be removed from stream (IV) using any apparatuses suitable for separating hydrogen from a gas stream comprising carbon monoxide, carbon dioxide, hydrogen and methane. Corresponding apparatuses are common knowledge to the person skilled in the art, for example pressure swing adsorption or permeation. Preferably, in the process of the invention, the hydrogen is separated off in the hydrogen recovery unit (A) by pressure swing adsorption.

In pressure swing adsorption, the gas to be separated is guided into an adsorbent-filled vessel under elevated pressure, generally in the range from 0.6 to 1 MPa abs. The components heavier than hydrogen are adsorbed, and hydrogen as light component is conducted out of the vessel in concentrated form. If the adsorber bed has been largely saturated with the heavier components, the gas to be separated, for further adsorption, is guided into another, likewise adsorbent-filled vessel, and the heavier components are released again by desorption from the previous vessel by lowering the pressure and removed separately as such. In this way, the previous vessel is regenerated again and prepared for a new cycle.

Since a particularly high level of cost and inconvenience would be required to separate off the hydrogen completely, the separation is generally incomplete. Typically, when the hydrogen recovery unit (H) is used, only 50% to 95%, preferably 60% and preferably 90%, of the hydrogen present in the gas stream is removed. Therefore, stream (IV), even after the separation of hydrogen, typically still comprises corresponding residual amounts of hydrogen.

The hydrogen separated off generally has a relatively high purity. The preferred pressure swing adsorption affords the hydrogen separated off generally in a purity of 90% to 100% by volume, preferably of 95% by volume, more preferably of 99% by volume and most preferably of 99.5% by volume.

Figure 4:
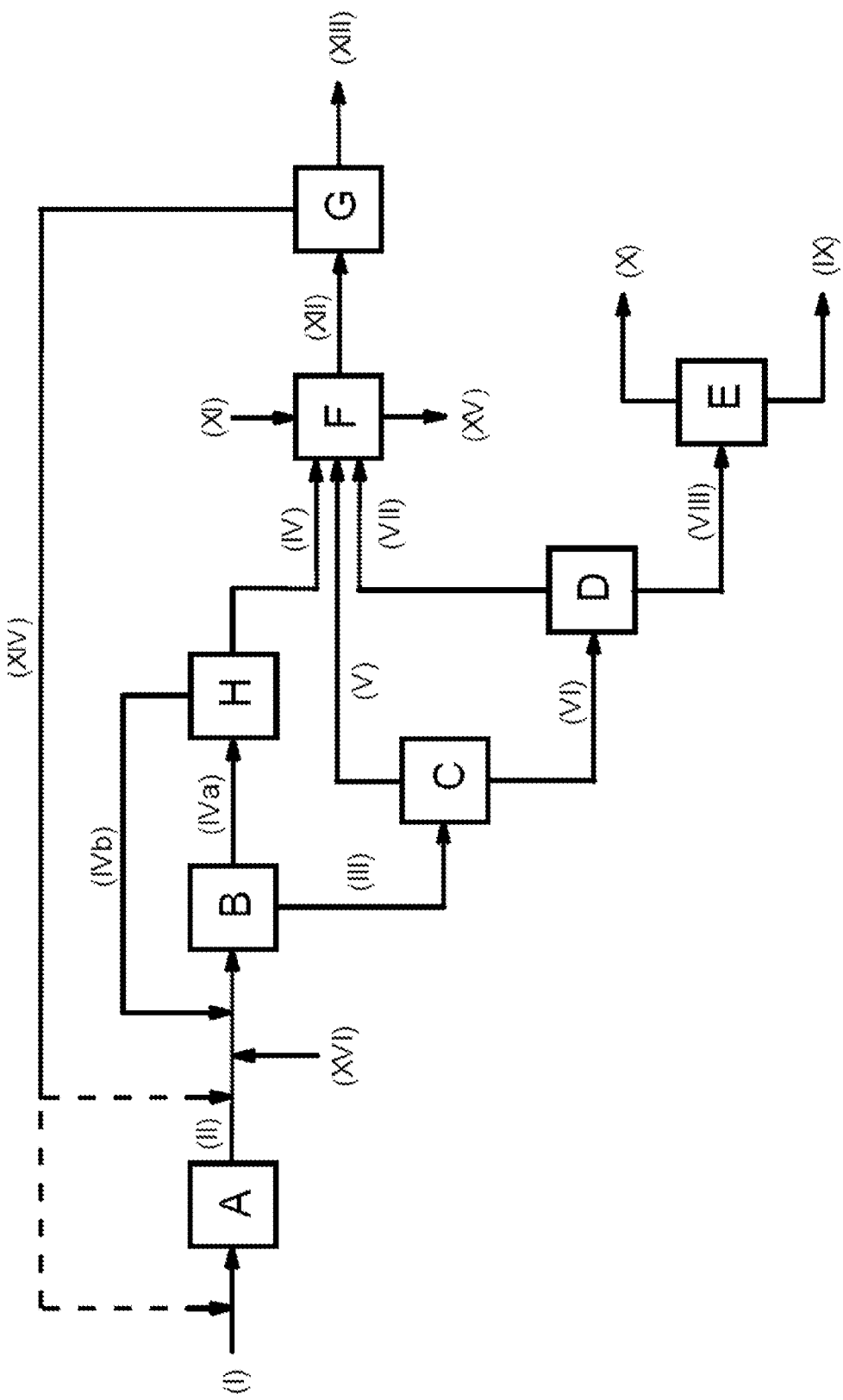
FIG. 4 shows a block diagram of a general embodiment in which additional hydrogen is supplied via stream (XVI).

An increase in the hydrogen content at the reactor inlet and hence in the stoichiometric number S at the reactor inlet is additionally also possible by adding further hydrogen. Preference is therefore given to a process in which the methanol synthesis unit (B) in stage (b) is supplied with further hydrogen (XVI) in addition to the hydrogen supplied via the synthesis gas. FIG. 4 shows a block diagram of a general embodiment in which additional hydrogen is supplied via stream (XVI).

Preferably, the further hydrogen (XVI) is fed to the synthesis gas compressor and then fed into the reactor together with the compressed synthesis gas. However, if the further hydrogen (XVI) is already under a correspondingly high pressure, it is of course also possible to feed it separately into the methanol synthesis reactor.

In order to avoid the accumulation of substances extraneous to the reaction and especially of inert gases in the methanol synthesis, it is desirable to feed in, as hydrogen (XVI), preferably hydrogen of maximum purity or at least hydrogen having only a low content of substances extraneous to the reaction. The hydrogen (XVI) fed in preferably has a hydrogen content of 80% by volume, more preferably of 90% by volume, even more preferably of 95% by volume, especially of 99% by volume and in particular of 99.5% by volume.

The hydrogen (XVI) fed in may in principle come from a wide variety of different sources. Examples include the supply of hydrogen from other production plants in which hydrogen is formed deliberately or as a by-product, for example from steamcrackers or refineries, from the processing of synthesis gas, from the cracking of hydrocarbons, for example the pyrolysis of methane and/or higher hydrocarbons, or from the electrolysis of water. Further examples of production plants in which hydrogen is formed include the conversion of butane-1,4-diol to γ-butyrolactone, the dehydrogenation of propane to propene, the dehydrogenation of methanol to formaldehyde, the dehydrogenation of cyclohexanol to cyclohexanone, and the dehydrogenation of cyclododecanol to cyclododecanone.

Particular preference is given to the use of hydrogen from renewable sources. In this connection, particular mention should be made of the electrolysis of water by solar, wind or water energy.

The amount of hydrogen (XVI) to be fed in is generally guided by the desired stoichiometric number S at the reactor inlet.

Even though it is preferable for the purposes of improved preparation of methanol in terms of energy, mass and the environment to increase the stoichiometric number S at the reactor inlet primarily first of all by utilizing the hydrogen present in the system via the hydrogen recovery unit (H) and only to supply additional hydrogen via stream (XVI) when required, it is of course also possible to supply additional hydrogen via stream (XVI) even without utilizing a hydrogen recovery unit. This would be of interest, for example, in the event of an oversupply of additional hydrogen and would dispense with the provision and operation of a hydrogen recovery unit.

The block diagram of a general embodiment of the process of the invention in which all three streams (IV), (V) and (VII) are guided to the combustion unit (F) is shown in FIG. 1. The general meanings of the apparatus units and apparatuses (A) to (G) and streams (I) to (XIV) have already been listed in the general description of the invention with reference to FIG. 1.

The description which follows relates to a preferred embodiment with the following characteristics:

(I) The synthesis gas production unit (A) is supplied with preferably methane-containing gas, for example, natural gas or biogas, via stream (I).

(A) Synthesis gas (II) is produced in the synthesis gas production unit (A) from the preferably methane-containing gas (I). For this purpose, preference is given to steam reforming, autothermal reforming, a combination of steam reforming and autothermal reforming, and the partial oxidation.

(B) The methanol synthesis unit (B) comprises a compressor for compression of the synthesis gas, a methanol synthesis reactor comprising a methanol synthesis catalyst for conversion of the synthesis gas to methanol, a condenser for condensing out crude methanol, and a corresponding conduit for recycling synthesis cycle gas. By condensation of the reaction mixture obtained, crude methanol (III) is obtained and conducted away. Uncondensed gas is conducted away as stream (IV).

(C) The expansion unit (C) comprises a vessel in which the crude methanol (III) separated off is expanded, forming what is called expansion gas (V) and degassed crude methanol (VI).

(D) The degassed crude methanol (VI) is worked up by distillation. In stage (d), for this purpose, low boilers (VII) are first removed, and methanol is further enriched in the bottom stream (VIII). Distillation apparatus (D) is typically a distillation column, also called low boiler column.

(E) What is called the purifying distillation of the methanol is effected in distillation apparatus (E). For energy-related reasons, the use of what is called a two-pressure distillation is particularly advantageous here. Pure methanol is obtained as stream (X), and high boilers are removed via the bottom as stream (IX).

(F) The combustion unit (F) comprises a combustion chamber. The process streams (IV), (V) and (VII) separated off are guided into it and combusted with supply of an oxygenous gas (XI) to give carbon dioxide. Owing to the advantages mentioned in the description, the use of pure oxygen as oxidizer is particularly preferred.

(G) In the carbon dioxide recovery unit (G), carbon dioxide is separated from the flue gas (XII) that has been removed from the combustion unit (F) and recycled via stream (XIV) to the synthesis gas production unit (A) and/or to the methanol synthesis unit (B). The dotted lines in stream (XIV) indicate the variants mentioned. In the case of recycling to the methanol synthesis unit (B), stream (XIV) is preferably fed to the synthesis gas compressor.

The carbon dioxide recovery unit (G) is preferably what is called a carbon dioxide gas scrubbing unit, in which carbon dioxide is selectively scrubbed out in an absorber in an aqueous solution of an organic amine to form the offgas stream (XIII) and subsequently released again in a desorber.

FIG. 2 is based on FIG. 1 and differs in that the combustion unit (F), as well as a combustion chamber, also comprises a condenser in which water is condensed out of the combustion gas and conducted away as stream (XV). This distinctly reduces the water content in the flue gas (XII) by a relatively simple measure and facilitates the subsequent recovery of the carbon dioxide.

FIG. 3 is based on FIG. 2 and differs in that, before stream (IV) is fed to the combustion unit (F), hydrogen is separated off in a hydrogen recovery unit (H). The hydrogen is preferably removed by pressure swing adsorption. The hydrogen removed is recycled as stream (IVb) to the methanol synthesis unit (B) and preferably added to the compressor therein.

FIG. 4 is based on FIG. 3 and differs in that additional hydrogen is supplied to the methanol synthesis unit (B) via stream (XVI).

Figure 5:
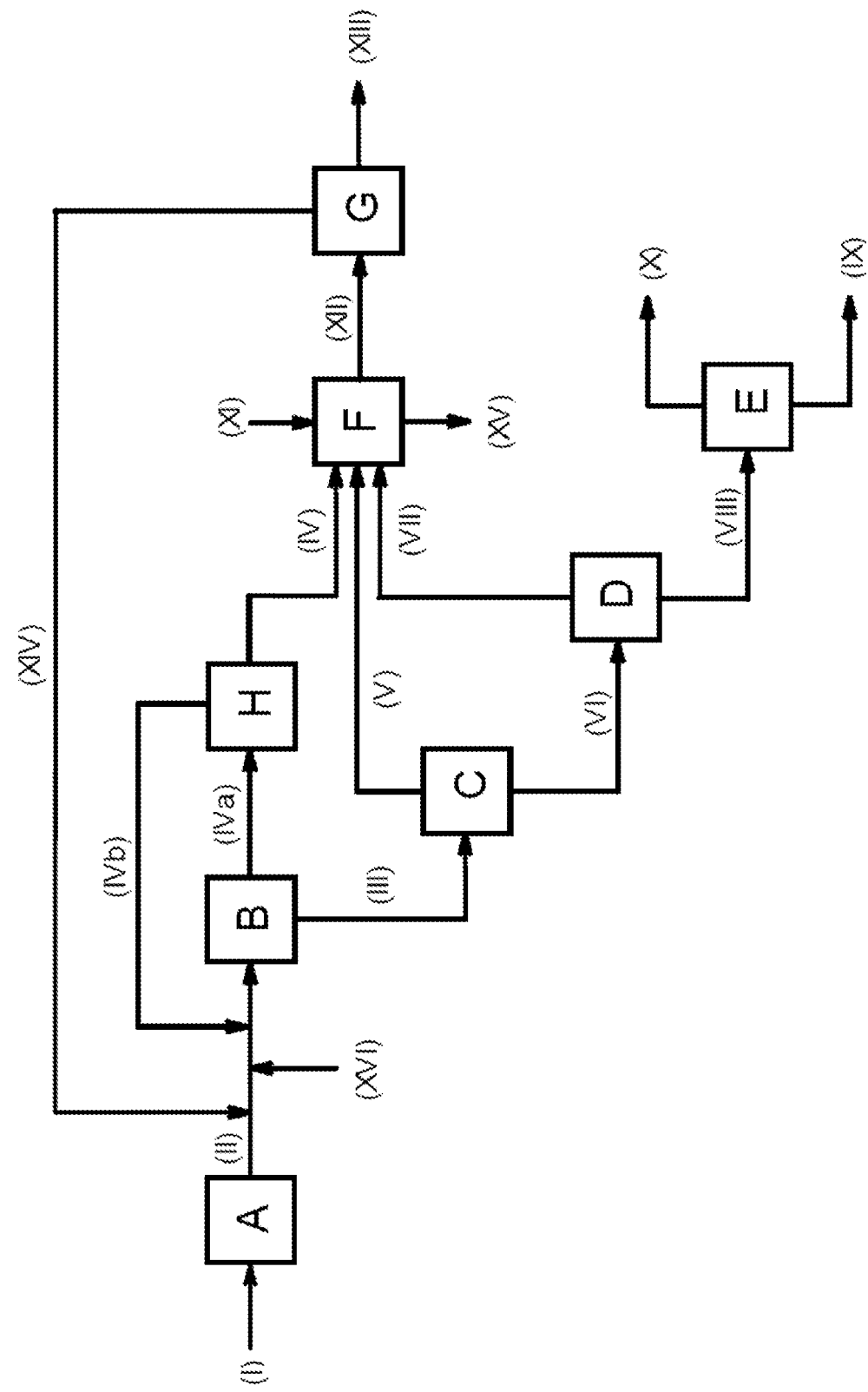
FIG. 5 shows a block diagram in which the carbon dioxide-enriched stream (XIV) is recycled to methanol synthesis unit (B).

FIG. 5 is based on FIG. 4 and differs in that the carbon dioxide-enriched stream (XIV) is recycled to the methanol synthesis unit (B).

The process of the invention enables the preparation of methanol from synthesis gas in a high yield and purity using the apparatuses and interconnections that are customary in the methanol synthesis processes, but with the crucial advantage of a virtually complete physical utilization of the carbon-containing components of value for methanol synthesis and with avoidance of emission of carbon dioxide. However, the virtually complete physical utilization of the carbon-containing components of value for methanol synthesis not only avoids the emission of carbon dioxide which is harmful to the climate, but also increases the yield of methanol. Owing to the use of the apparatuses and interconnections that are customary in the methanol synthesis process for the actual methanol synthesis and methanol workup, the process of the invention can also be retrofitted without difficulty in existing methanol synthesis plants. Owing to the absolute amounts, there is generally no requirement for any technical interventions, modifications or supplementations in the synthesis gas production even in the case of recycling of the carbon dioxide separated off for synthesis gas production. The apparatuses and process stages required for performance of the process of the invention, whether for retrofitting of existing methanol synthesis plants or the new construction of methanol synthesis plants, can be readily designed and installed by the person skilled in the art with common knowledge in the art. The cost and inconvenience associated with the installation and the operation of the components required is relatively low. The process of the invention at the same time also very elegantly solves the problem of the discharge of unwanted inert gases via the offgas stream of the carbon dioxide recovery unit. By supply of hydrogen obtained in a climate-neutral manner, which has been obtained, for example, by electrolysis of water on the basis of solar, wind or water energy, it is additionally possible to further increase the sustainability of the process of the invention.

EXAMPLES

Interconnection 1 Comparative Examples

Figure 6:
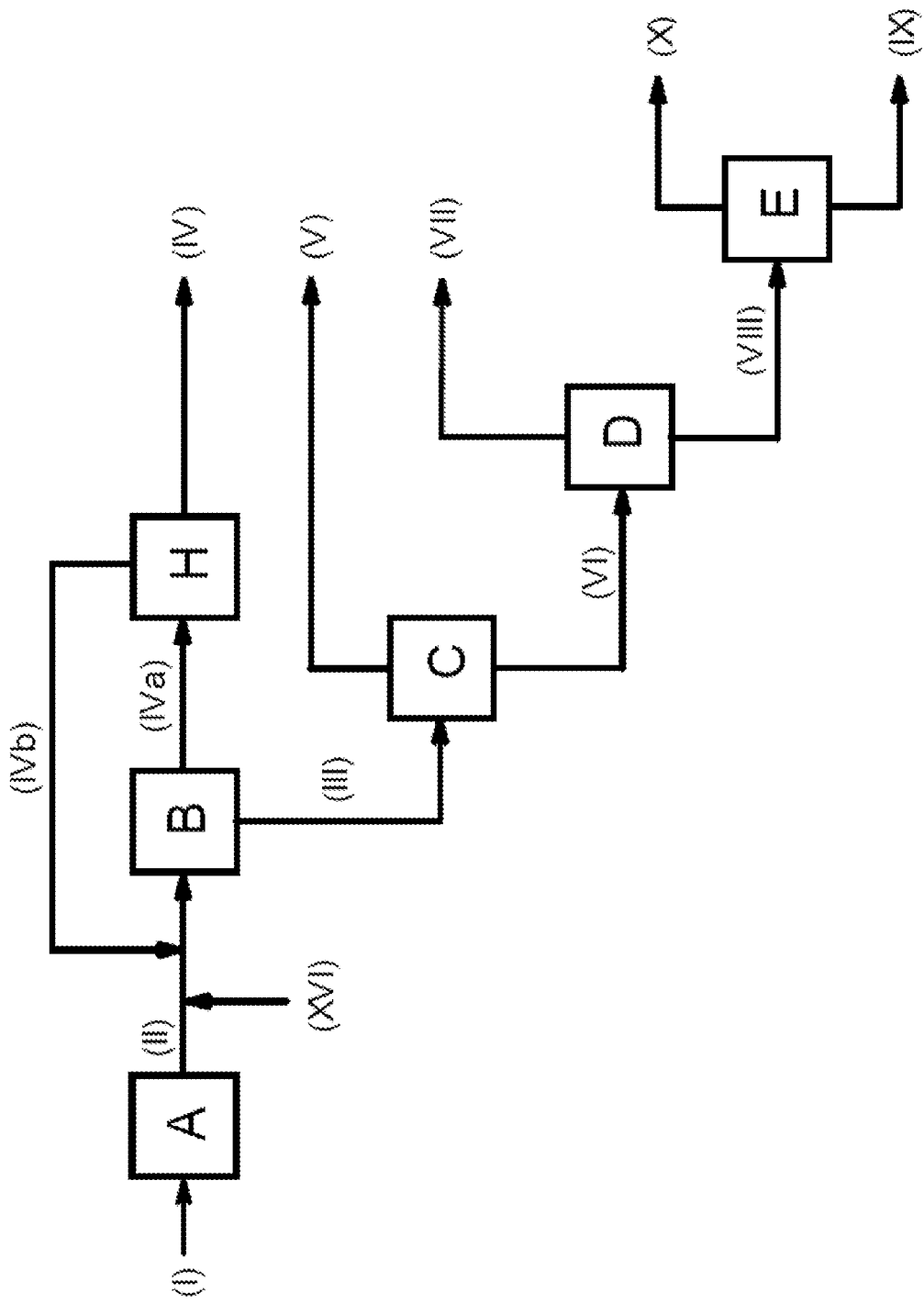
FIG. 6 shows a simplified block diagram of an interconnection for preparation of methanol according to the prior art.

FIG. 6 shows a simplified block diagram of an interconnection for preparation of methanol according to the prior art. The labels therein have the following meanings:
(A) synthesis gas production unit
(B) methanol synthesis unit
(C) expansion unit (low pressure expansion)
(D) low boiler column
(E) pure methanol column
(H) pressure swing adsorption
(I) natural gas
(II) synthesis gas
(IVb) recovered hydrogen from pressure swing adsorption (H)
(IV) offgas from pressure swing adsorption (H)
(V) expansion gas from expansion unit (C)
(VII) low boiler stream from low boiler column (D)
(IX) high boiler stream from pure methanol column (E)
(X) pure methanol
(XVI) hydrogen ("fresh hydrogen")

In addition, the interconnection has the following further features:
The methanol synthesis unit (B) comprises a compressor, a reactor, a condenser and a synthesis gas circuit.

The hydrogen recovery rate of the pressure swing adsorption (H) is 83%.

The fresh hydrogen (XVI) comprises >99.5% by volume of hydrogen.

Unless stated otherwise in the respective comparative example, hydrogen is recovered via the pressure swing adsorption (H) and recycled via stream (IVb) to the methanol synthesis unit (B), and fresh hydrogen is supplied via stream (XVI). Streams (IV), (V) and (VII) are each discharged from the interconnection.

Interconnection 2 Inventive Examples

FIG. 5 shows a simplified block diagram of an interconnection for the inventive preparation of methanol. The labels therein have the following meanings:
(A) synthesis gas production unit
(B) methanol synthesis unit
(C) expansion unit
(D) low boiler column
(E) pure methanol column
(F) combustion unit
(G) carbon dioxide recovery unit
(H) pressure swing adsorption
(I) natural gas
(II) synthesis gas
(IVb) recovered hydrogen from pressure swing adsorption (H)
(IV) offgas from pressure swing adsorption (H)
(V) expansion gas from expansion unit (C)
(VII) low boiler stream from low boiler column (D)
(IX) high boiler stream from pure methanol column (E)
(X) pure methanol
(XI) oxygenous gas
(XII) flue gas
(XIII) offgas from carbon dioxide recovery unit (G)
(XIV) carbon dioxide-enriched stream from carbon dioxide recovery unit (G)
(XV) condensed water from combustion unit (F)
(XVI) hydrogen ("fresh hydrogen")

In addition, the interconnection has the following further features:

The methanol synthesis unit (B) comprises a compressor, a reactor, a condenser and a synthesis gas circuit.

The combustion unit (F) comprises a combustion chamber and a condenser.

The combustible components are converted to carbon dioxide and water in the combustion chamber to an extent of >99%.

The carbon dioxide recovery rate of the carbon dioxide recovery unit (G) is >99%.

The hydrogen recovery rate of the pressure swing adsorption (H) is 83%.

The fresh hydrogen (XVI) comprises >99.5% by volume of hydrogen.

Streams (IV), (V) and (VII) are combusted in the combustion unit (F) with supply of pure oxygen, and the flue gas (XII) obtained is supplied to the carbon dioxide recovery unit (G) for recovery of carbon dioxide. Recovered carbon dioxide is recycled as stream (XIV) to the methanol synthesis unit (B). The offgas from the carbon dioxide recovery unit (G) is discharged from the interconnection.

Example 1 Comparative

Comparative example 1 relates to methanol synthesis from synthesis gas that comes from the partial oxidation of natural gas (I). The underlying interconnection is shown in FIG. 6 and is described in detail as "interconnection 1". Table 1 shows the composition of the synthesis gas (II), which corresponds to a typical composition for synthesis gas from the partial oxidation of natural gas. This gives a stoichiometric number S of 1.625. In order, however, to establish a stoichiometric number S of 3.40 at the reactor inlet, it is necessary, in addition to the hydrogen present in the synthesis gas (II), the hydrogen recycled within the methanol synthesis unit (B) via the synthesis cycle gas and the hydrogen recycled from the pressure swing adsorption (H), to supply another 250.1 m$^3$ (STP) of fresh hydrogen (XVI) per tonne of pure methanol produced (stream (X)). The content of inerts ($CH_4$, $H_2O$, $N_2$, Ar) at the reactor inlet is 24.4% by volume. Conversion by heterogeneous catalysis over a copper-containing methanol synthesis catalyst at 235° C. and a pressure of 7.7 MPa abs and the further workup of the reaction mixture according to the simplified block diagram of FIG. 6 results in streams (IV), (V) (after expansion to 0.6 MPa abs at 40° C.) and (VII) with the amounts and compositions specified in table 1.

Owing to the discharge of streams (IV), (V) and (VII) from the interconnection, these remain unutilized for further methanol synthesis. In processes according to the prior art, these are typically supplied solely to a thermal utilization, i.e. not physically utilized. Thus, in the present comparative example 1, 1983 m$^3$ (STP) of synthesis gas (II) are required for the preparation of one tonne of pure methanol (stream (X)).

Example 2 Inventive

Inventive example 2 likewise relates to methanol synthesis from synthesis gas that comes from the partial oxidation of natural gas (I). The underlying interconnection is shown in FIG. 5 and is described in detail as "interconnection 2". Table 2 shows the composition of the synthesis gas (II), which corresponds to a typical composition for synthesis gas from the partial oxidation of natural gas and is identical to that from example 1. Thus, in inventive example 2 as well, the stoichiometric number S of the synthesis gas (II) is 1.625. In order to establish a stoichiometric number S of 3.40 at the reactor inlet in example 2 as well, it is necessary, in addition to the hydrogen present in the synthesis gas (II), the hydrogen recycled within the methanol synthesis unit (B) via the synthesis cycle gas and the hydrogen recycled from the pressure swing adsorption (H), to supply another 318.0 m$^3$ (STP) of fresh hydrogen (XVI) per tonne of pure methanol produced (stream (X)). The content of inerts ($CH_4$, $H_2O$, $N_2$, Ar) at the reactor inlet is 24.2% by volume. Conversion by heterogeneous catalysis over a copper-containing methanol synthesis catalyst at 235° C. and a pressure of 7.7 MPa abs and the further workup of the reaction mixture according to the simplified block diagram of FIG. 5 results in streams (IV), (V) (after expansion to 0.6 MPa abs at 40° C.) and (VII) with the amounts and compositions specified in table 2. By contrast with comparative example 1, however, these are not discharged unutilized from the interconnection, but combusted in accordance with the invention in the combustion unit (F) with supply of pure oxygen (XI). After condensation of 88.6% of the water present and discharge thereof as stream (XV), the carbon dioxide-containing flue gas (XII) is fed to a carbon dioxide recovery unit (G). >99% of the carbon dioxide present in the flue gas (XII) is isolated therein as stream (XIV) and recycled to the methanol synthesis unit (B).

Only 1905 m³ (STP) of synthesis gas (II) are thus required for the preparation of one tonne of pure methanol (stream (X)) in inventive example 2.

By comparison with comparative example 1 in which streams (IV), (V) and (VII) are discharged unutilized from the interconnection, the process of the invention enables, in example 2, the substantial utilization of the carbon monoxide, carbon dioxide, methane and dimethyl ether components of value present in these streams for the further synthesis of methanol.

Specifically, although this leads to an additional consumption of 67.9 m³ (STP) of fresh hydrogen per tonne of pure methanol (stream (X)), it spares the use of 78 m³ (STP) of synthesis gas (II) per tonne of pure methanol (stream (X)) and hence the equivalent amount of natural gas, and also the emission of additional carbon dioxide that would otherwise have been formed via a purely thermal utilization of streams (IV), (V) and (VII) in the case of the prior art interconnection.

The inventive removal and recycling of the carbon dioxide via stream (XIV) increases the carbon dioxide content at the reactor inlet from 3.0% by volume in comparative example 1 to 3.9% by volume in inventive example 2, but is still within a range for which the methanol synthesis catalysts typically used are designed.

Example 3 Comparative

Comparative example 3 relates to methanol synthesis from synthesis gas that comes from the autothermal reforming of natural gas. The underlying interconnection is shown in FIG. 6 and is described in detail as "interconnection 1". Table 3 shows the composition of the synthesis gas (II), which corresponds to a typical composition for synthesis gas from the autothermal reforming of natural gas. This gives a stoichiometric number S of 1.765. In order, however, to establish a stoichiometric number S of 3.40 at the reactor inlet, it is necessary, in addition to the hydrogen present in the synthesis gas (II), the hydrogen recycled within the methanol synthesis unit (B) via the synthesis cycle gas and the hydrogen recycled from the pressure swing adsorption (H), to supply another 128.7 m³ (STP) of fresh hydrogen (XVI) per tonne of pure methanol produced (stream (X)). The content of inerts ($CH_4$, $H_2O$, $N_2$, Ar) at the reactor inlet is 24.8% by volume. Conversion by heterogeneous catalysis over a copper-containing methanol synthesis catalyst at 235° C. and a pressure of 7.7 MPa abs and the further workup of the reaction mixture according to the simplified block diagram of FIG. 6 results in streams (IV), (V) (after expansion to 0.6 MPa abs at 40° C.) and (VII) with the amounts and compositions specified in table 3.

Owing to the discharge of streams (IV), (V) and (VII) from the interconnection, these remain unutilized for further methanol synthesis. In processes according to the prior art, these are typically supplied solely to a thermal utilization, i.e. not physically utilized. Thus, in the present comparative example 3, 2255 m³ (STP) of synthesis gas (II) are required for the preparation of one tonne of pure methanol (stream (X)).

Example 4 Inventive

Inventive example 4 likewise relates to methanol synthesis from synthesis gas that comes from the autothermal reforming of natural gas. The underlying interconnection is shown in FIG. 5 and is described in detail as "interconnection 2". Table 4 shows the composition of the synthesis gas (II), which corresponds to a typical composition for synthesis gas from the autothermal reforming of natural gas and is identical to that from example 3. Thus, in inventive example 4 as well, the stoichiometric number S of the synthesis gas (II) is 1.765. In order to establish a stoichiometric number S of 3.40 at the reactor inlet in example 4 as well, it is necessary, in addition to the hydrogen present in the synthesis gas (II), the hydrogen recycled within the methanol synthesis unit (B) via the synthesis cycle gas and the hydrogen recycled from the pressure swing adsorption (H), to supply another 273.1 m³ (STP) of fresh hydrogen (XVI) per tonne of pure methanol produced (stream (X)). The content of inerts ($CH_4$, $H_2O$, $N_2$, Ar) at the reactor inlet is 23.7% by volume. Conversion by heterogeneous catalysis over a copper-containing methanol synthesis catalyst at 235° C. and a pressure of 7.7 MPa abs and the further workup of the reaction mixture according to the simplified block diagram of FIG. 5 results in streams (IV), (V) (after expansion to 0.6 MPa abs at 40° C.) and (VII) with the amounts and compositions specified in table 4. By contrast with comparative example 3, however, these are not discharged unutilized from the interconnection, but combusted in accordance with the invention in the combustion unit (F) with supply of pure oxygen (XI). After condensation of 93.5% of the water present and discharge thereof as stream (XV), the carbon dioxide-containing flue gas (XII) is fed to a carbon dioxide recovery unit (G). >99% of the carbon dioxide present in the flue gas (XII) is isolated therein as stream (XIV) and recycled to the methanol synthesis unit (B).

Only 2093 m³ (STP) of synthesis gas (II) are thus required for the preparation of one tonne of pure methanol (stream (X)) in inventive example 4.

By comparison with comparative example 3 in which streams (IV), (V) and (VII) are discharged unutilized from the interconnection, the process of the invention enables, in example 4, the substantial utilization of the carbon monoxide, carbon dioxide, methane and dimethyl ether components of value present in these streams for the further synthesis of methanol. Specifically, although this leads to an additional consumption of 144.4 m³ (STP) of fresh hydrogen per tonne of pure methanol (stream (X)), it spares the use of 162 m³ (STP) of synthesis gas (II) per tonne of pure methanol (stream (X)) and hence the equivalent amount of natural gas, and also the emission of additional carbon dioxide that would otherwise have been formed via a purely thermal utilization of streams (IV), (V) and (VII) in the case of the prior art interconnection.

The inventive removal and recycling of the carbon dioxide via stream (XIV) increases the carbon dioxide content at the reactor inlet from 6.6% by volume in comparative example 3 to 7.4% by volume in inventive example 4, but is still within a range for which the methanol synthesis catalysts typically used are designed.

Example 5 Comparative

Comparative example 5 relates to methanol synthesis from synthesis gas that comes from a combination of steam reforming and autothermal reforming of natural gas. Table 5 shows the composition of the synthesis gas (II), which corresponds to a typical composition for synthesis gas from combined steam and autothermal reforming of natural gas. This gives a stoichiometric number S of 2.007. Since the hydrogen present in the synthesis gas (II) together with the hydrogen recycled via the synthesis cycle gas is already sufficient to establish a stoichiometric number S of 3.40 at the reactor inlet, there is no requirement in the present comparative example 5 either for recovery of hydrogen by a hydrogen recovery unit with recycling of the hydrogen recovered or for supply of fresh hydrogen. The interconnection underlying comparative example 5 is therefore likewise based on the interconnection shown in FIG. 6 and described in detail as "interconnection 1", but has neither a hydrogen recovery unit (H) with downstream recycling of the hydrogen nor supply of fresh hydrogen (XVI). The content of inerts (CH$_4$, H$_2$O, N$_2$, Ar) at the reactor inlet is 24.4% by volume. Conversion by heterogeneous catalysis over a copper-containing methanol synthesis catalyst at 235° C. and a pressure of 7.7 MPa abs and the further workup of the reaction mixture according to the simplified block diagram of FIG. 6 results in streams (IV), (V) (after expansion to 0.6 MPa abs at 40° C.) and (VII) with the amounts and compositions specified in table 5.

Owing to the discharge of streams (IV), (V) and (VII) from the interconnection, these remain unutilized for further methanol synthesis. In processes according to the prior art, these are typically supplied solely to a thermal utilization, i.e. not physically utilized. Thus, in the present comparative example 5, 2478 m$^3$ (STP) of synthesis gas (II) are required for the preparation of one tonne of pure methanol (stream (X)).

Example 6 Inventive

Inventive example 6 likewise relates to methanol synthesis from synthesis gas that comes from a combination of steam reforming and autothermal reforming of natural gas. The underlying interconnection is shown in FIG. 5 and is described in detail as "interconnection 2". Table 6 shows the composition of the synthesis gas (II), which corresponds to a typical composition for synthesis gas from combined steam and autothermal reforming of natural gas and is identical to that from example 5. Thus, in inventive example 6 as well, the stoichiometric number S of the synthesis gas (II) is 2.007. Unlike in comparative example 5, however, in inventive example 6, in order to establish a stoichiometric number S of 3.40 at the reactor inlet, in addition to the hydrogen present in the synthesis gas (II) and the hydrogen recycled within the methanol synthesis unit (B) via the synthesis cycle gas, it is also necessary to supply hydrogen from the pressure swing adsorption (H) and 156.1 m$^3$ (STP) of fresh hydrogen (XVI) per tonne of pure methanol produced (stream (X)). The content of inerts (CH$_4$, H$_2$O, N$_2$, Ar) at the reactor inlet is 24.9% by volume. Conversion by heterogeneous catalysis over a copper-containing methanol synthesis catalyst at 235° C. and a pressure of 7.7 MPa abs and the further workup of the reaction mixture according to the simplified block diagram of FIG. 5 results in streams (IV), (V) (after expansion to 0.6 MPa abs at 40° C.) and (VII) with the amounts and compositions specified in table 6. By contrast with comparative example 5, however, these are not discharged unutilized from the interconnection, but combusted in accordance with the invention in the combustion unit (F) with supply of pure oxygen (XI). After condensation of 94.2% of the water present and discharge thereof as stream (XV), the carbon dioxide-containing flue gas (XII) is fed to a carbon dioxide recovery unit (G). >99% of the carbon dioxide present in the flue gas (XII) is isolated therein as stream (XIV) and recycled to the methanol synthesis unit (B).

Only 2238 m$^3$ (STP) of synthesis gas (II) are thus required for the preparation of one tonne of pure methanol (stream (X)) in inventive example 6.

When a flue gas scrubbing operation is used as carbon dioxide recovery unit (G) with an absorption column and a desorption column that are connected to one another via a crossflow heat exchanger, and which is operated with an aminic absorbent as absorption liquid, an absorbent circulation stream of 2.71 t of absorbent per tonne of pure methanol (stream (X)) and a regeneration energy for regeneration of the carbon dioxide-laden absorbent of 0.087 MW per tonne of pure methanol (stream (X)) are required for said carbon dioxide recovery of >99%.

By comparison with comparative example 5 in which streams (IV), (V) and (VII) are discharged unutilized from the interconnection, the process of the invention enables, in example 6, the substantial utilization of the carbon monoxide, carbon dioxide, methane and dimethyl ether components of value present in these streams for the further synthesis of methanol. Specifically, although this leads to an additional consumption of 156.1 m$^3$ (STP) of fresh hydrogen per tonne of pure methanol (stream (X)), it spares the use of 240 m$^3$ (STP) of synthesis gas (II) per tonne of pure methanol (stream (X)) and hence the equivalent amount of natural gas, and also the emission of additional carbon dioxide that would otherwise have been formed via a purely thermal utilization of streams (IV), (V) and (VII) in the case of the prior art interconnection.

The inventive removal and recycling of the carbon dioxide via stream (XIV) increases the carbon dioxide content at the reactor inlet from 6.8% by volume in comparative example 5 to 7.7% by volume in inventive example 6, but is still within a range for which the methanol synthesis catalysts typically used are designed.

Example 7 Comparative

Comparative example 7 corresponds to inventive example 6, but differs in that streams (IV), (V) and (VII) are combusted in the combustion unit (F) with supply of air (stream (XI)) rather than pure oxygen and then 61.2% of the water present is condensed out. This increases the amount of flue gas (XII) formed from around 92 m$^3$ (STP) (example 7) significantly to around 649 m$^3$ (STP) per tonne of pure methanol (stream (X)), and there is a distinct fall in the content of carbon dioxide in the flue gas (XII) from around 77% by volume to only around 11% by volume. Correspondingly, there is also a rise in the absorber area required in the absorption column to about 3.8 times the area. In addition, there is an increase in the absorbent circulation stream from 2.71 t to 4.93 t per tonne of pure methanol (stream (X)) and in the regeneration energy required from 0.087 MW to 0.12 MW per tonne of pure methanol (stream (X)). A tabular overview thereof can be found in table 7.

The use of pure oxygen as oxygenous gas (XI) in the combustion unit (F) allows the flue gas scrubbing to be designed and operated much more efficiently compared to the use of air.

TABLE 1

| | Data for example I (comparative) | | | | |
|---|---|---|---|---|---|
| | Synthesis gas (II) | Fresh hydrogen (XVI) | (IV) | (V) | (VII) |
| Amount [m$^3$ (STP)/t methanol] | 1983 | 250.1 | 16.8 | 10.9 | 10.7 |
| CO [% by vol.] | 33.91 | | 4.50 | 2.77 | 0.11 |
| CH$_3$OH [% by vol.] | 0 | | 1.15 | 5.85 | 6.76 |
| H$_2$ [% by vol.] | 62.20 | >99.5 | 16.37 | 19.02 | 0.43 |
| CH$_4$ [% by vol.] | 0.44 | | 27.86 | 30.13 | 7.07 |
| CH$_3$OCH$_3$ [% by vol.] | 0 | | 0 | 0.02 | 0.30 |
| CO$_2$ [% by vol.] | 2.70 | | 6.27 | 21.66 | 44.86 |
| H$_2$O [% by vol.] | 0.29 | | 0.04 | 0.14 | 12.11 |
| N$_2$ [% by vol.] | 0.38 | | 38.13 | 10.22 | 0.42 |
| O$_2$ [% by vol.] | 0 | | 0 | 0 | 0 |
| Ar [% by vol.] | 0.08 | | 5.68 | 4.48 | 0.68 |
| Stoichiometric number S | 1.625 | | | | |

TABLE 2

Data for example 2 (inventive)

| | Synthesis gas (II) | Fresh hydrogen (XVI) | (IV) | (V) | (VII) | (XII) | (XIII) | (XIV) |
|---|---|---|---|---|---|---|---|---|
| Amount [m$^3$ (STP)/t methanol] | 1905 | 318.0 | 16.2 | 11.6 | 11.6 | 43.5 | 12.6 | 30.8 |
| CO [% by vol.] | 33.91 | | 3.87 | 2.27 | 0.08 | 0 | 0 | 0 |
| CH$_3$OH [% by vol.] | 0 | | 1.09 | 5.68 | 6.05 | 0 | 0 | 0 |
| H$_2$ [% by vol.] | 62.20 | >99.5 | 16.69 | 18.15 | 0.36 | 0 | 0 | 0 |
| CH$_4$ [% by vol.] | 0.44 | | 27.48 | 28.01 | 5.78 | 0 | 0 | 0 |
| CH$_3$OCH$_3$ [% by vol] | 0 | | 0 | 0.02 | 0.28 | 0 | 0 | 0 |
| CO$_2$ [% by vol.] | 2.70 | | 7.49 | 26.36 | 49.39 | 64.32 | 0.44 | 90.51 |
| H$_2$O [% by vol.] | 0.29 | | 0.05 | 0.20 | 12.47 | 7.47 | 2.57 | 9.48 |
| N$_2$ [% by vol.] | 0.38 | | 37.75 | 9.36 | 0.34 | 17.49 | 60.14 | 0.01 |
| O$_2$ [% by vol.] | 0 | | 0 | 0 | 0 | 7.21 | 24.77 | 0.004 |
| Ar [% by vol.] | 0.08 | | 5.59 | 4.17 | 0.56 | 3.51 | 12.08 | 0.001 |
| Stoichiometric number S | 1.625 | | | | | | | |

TABLE 3

Data for example 3 (comparative)

| | Synthesis gas (II) | Fresh hydrogen (XVI) | (IV) | (V) | (VII) |
|---|---|---|---|---|---|
| Amount [m$^3$ (STP)/t methanol] | 2255 | 128.7 | 40.3 | 15.1 | 12.6 |
| CO [% by vol.] | 24.13 | | 3.28 | 1.02 | 0.03 |
| CH$_3$OH [% by vol.] | 0 | | 1.04 | 5.10 | 6.87 |
| H$_2$ [% by vol.] | 65.71 | >99.5 | 16.99 | 11.98 | 0.18 |
| CH$_4$ [% by vol.] | 1.22 | | 52.43 | 36.95 | 5.65 |
| CH$_3$OCH$_3$ [% by vol.] | 0 | | 0 | 0.03 | 0.24 |
| CO$_2$ [% by vol.] | 8.36 | | 10.80 | 34.24 | 53.55 |
| H$_2$O [% by vol.] | 0.28 | | 0.09 | 0.38 | 12.17 |
| N$_2$ [% by vol.] | 0.19 | | 9.98 | 1.57 | 0.04 |
| O$_2$ [% by vol.] | 0 | | 0 | 0 | 0 |
| Ar [% by vol.] | 0.12 | | 5.39 | 2.86 | 0.30 |
| Stoichiometric number S | 1.765 | | | | |

TABLE 4

Data for example 4 (inventive)

| | Synthesis gas (II) | Fresh hydrogen (XVI) | (IV) | (V) | (VII) | (XII) | (XIII) | (XIV) |
|---|---|---|---|---|---|---|---|---|
| Amount [m$^3$ (STP)/t methanol] | 2093 | 273.1 | 38.8 | 14.6 | 13.0 | 70.4 | 12.9 | 57.5 |
| CO [% by vol.] | 24.13 | | 3.18 | 0.89 | 0.02 | 0 | 0 | 0 |
| CH$_3$OH [% by vol.] | 0 | | 1.02 | 4.91 | 7.38 | 0 | 0 | 0 |
| H$_2$ [% by vol.] | 65.71 | >99.5 | 17.76 | 11.79 | 0.16 | 0 | 0 | 0 |
| CH$_4$ [% by vol.] | 1.22 | | 51.15 | 34.17 | 4.71 | 0 | 0 | 0 |
| CH$_3$OCH$_3$ [% by vol.] | 0 | | 0 | 0.03 | 0.23 | 0 | 0 | 0 |
| CO$_2$ [% by vol.] | 8.36 | | 11.90 | 37.48 | 55.09 | 75.72 | 0.83 | 92.50 |
| H$_2$O [% by vol.] | 0.28 | | 0.10 | 0.44 | 11.93 | 6.80 | 3.71 | 7.49 |
| N$_2$ [% by vol.] | 0.19 | | 9.68 | 1.41 | 0.03 | 6.69 | 36.54 | 0.002 |
| O$_2$ [% by vol.] | 0 | | 0 | 0 | 0 | 7.11 | 38.82 | 0.003 |
| Ar [% by vol.] | 0.12 | | 5.21 | 2.65 | 0.26 | 3.68 | 20.09 | 0.001 |
| Stoichiometric number S | 1.765 | | | | | | | |

TABLE 5

Data for example 5 (comparative)

| | Synthesis gas (II) | Fresh hydrogen (XVI) | (IV) | (V) | (VII) |
|---|---|---|---|---|---|
| Amount [m$^3$ (STP)/t methanol] | 2478 | 0 | 119.1 | 15.4 | 12.6 |
| CO [% by vol.] | 21.52 | | 1.76 | 0.95 | 0.02 |
| CH$_3$OH [% by vol.] | 0 | | 0.57 | 5.04 | 6.39 |
| H$_2$ [% by vol.] | 67.94 | | 55.27 | 11.64 | 0.17 |
| CH$_4$ [% by vol.] | 1.79 | | 31.29 | 38.83 | 5.81 |
| CH$_3$OCH$_3$ [% by vol.] | 0 | | 0 | 0.03 | 0.24 |
| CO$_2$ [% by vol.] | 8.23 | | 6.06 | 34.80 | 53.97 |
| H$_2$O [% by vol.] | 0.26 | | 0.05 | 0.40 | 12.38 |
| N$_2$ [% by vol.] | 0.17 | | 3.45 | 0.95 | 0.02 |
| O$_2$ [% by vol.] | 0 | | 0 | 0 | 0 |
| Ar [% by vol.] | 0.09 | | 1.56 | 1.46 | 0.15 |
| Stoichiometric number S | 2.007 | | | | |

TABLE 6

Data for example 6 (inventive)

| | Synthesis gas (II) | Fresh hydrogen (XVI) | (IV) | (V) | (VII) | (XII) | (XIII) | (XIV) |
|---|---|---|---|---|---|---|---|---|
| Amount [m³ (STP)/t methanol] | 2238 | 156.1 | 58.7 | 15.0 | 12.8 | 92.2 | 15.8 | 76.4 |
| CO [% by vol.] | 21.52 | | 3.09 | 0.77 | 0.02 | 0 | 0 | 0 |
| $CH_3OH$ [% by vol.] | 0 | | 1.01 | 4.81 | 6.96 | 0 | 0 | 0 |
| $H_2$ [% by vol.] | 67.94 | >99.5 | 17.07 | 10.76 | 0.14 | 0 | 0 | 0 |
| $CH_4$ [% by vol.] | 1.79 | | 57.57 | 37.05 | 4.97 | 0 | 0 | 0 |
| $CH_3OCH_3$ [% by vol.] | 0 | | 0 | 0.03 | 0.23 | 0 | 0 | 0 |
| $CO_2$ [% by vol.] | 8.23 | | 11.92 | 37.51 | 55.06 | 76.85 | 0.89 | 92.60 |
| $H_2O$ [% by vol.] | 0.26 | | 0.10 | 0.47 | 12.13 | 6.80 | 3.96 | 7.39 |
| $N_2$ [% by vol.] | 0.17 | | 6.37 | 0.88 | 0.02 | 5.38 | 31.30 | 0.002 |
| $O_2$ [% by vol.] | 0 | | 0 | 0 | 0 | 8.66 | 50.41 | 0.004 |
| Ar [% by vol.] | 0.09 | | 2.87 | 1.42 | 0.14 | 2.31 | 13.44 | 0.001 |
| Stoichiometric number S | 2.007 | | | | | | | |

TABLE 7

Comparison of examples 6 and 7

| | Example 6 (inventive) | Example 7 (comparative) |
|---|---|---|
| Stream (XII) [m³ (STP)/t methanol] | 92 | 649 |
| $CO_2$ [% by vol.] | 77 | 11 |
| Absorbent circulation stream [t absorption liquid/t methanol] | 2.71 | 4.93 |
| Regeneration energy [MW/t methanol] | 0.087 | 0.12 |

The invention claimed is:

1. A process for preparing methanol by
(a) producing a synthesis gas comprising carbon monoxide, carbon dioxide and hydrogen from a carbonaceous feedstock in a synthesis gas production unit;
(b) feeding the synthesis gas from step (a) to a methanol synthesis unit and converting it at a temperature of 150 to 300° C. and a pressure of 5 to 10 MPa abs in the presence of a methanol synthesis catalyst to a reaction mixture containing methanol, water, carbon monoxide, carbon dioxide, hydrogen, dimethyl ether and methane, condensing a methanol- and water-enriched crude methanol stream out of said reaction mixture, and conducting the crude methanol stream and a gaseous stream comprising carbon monoxide, carbon dioxide, hydrogen and methane out of the methanol synthesis unit;
(c) expanding the crude methanol stream from step (b) in an expansion unit to a pressure of 0.1 to 2 MPa abs, and obtaining an expansion gas comprising carbon dioxide and methane and a degassed crude methanol stream enriched with methanol and water;
(d) separating a carbon dioxide- and dimethyl ether-comprising low boiler stream by distillation from the degassed crude methanol stream from step (c) in a distillation apparatus, and obtaining a methanol- and water-enriched bottom stream; and
(e) separating a water-containing high boiler stream from the bottom stream from step (d) in a further distillation apparatus, and obtaining methanol by distillation as an output stream,
which comprises
(f) feeding the carbon monoxide, carbon dioxide, dimethyl ether and methane components of value in the degassed crude methanol stream and in at least one of the expansion gas and the low boiler steam to a combustion unit and combusting them therein with supply of an oxygenous gas having an oxygen content of 30% to 100% by volume, forming carbon dioxide-containing flue gas;
(g) separating a carbon dioxide-enriched stream from the carbon dioxide-containing flue gas from step (f) in a carbon dioxide recovery unit to form an offgas stream; and
(h) recycling the carbon dioxide-enriched stream separated off in the carbon dioxide recovery unit from step (g) to the synthesis gas production unit of step (a) and/or to the methanol synthesis unit of step (b).

2. The process according to claim 1, wherein the hydrocarbonaceous feedstock used in step (a) is natural gas, biogas, coal, wood, plastics, mineral oil, bionaphtha or hydrocarbonaceous streams from mineral oil or natural gas processing, from chemical production processes, from renewable raw materials or from plastics recycling.

3. The process according to claim 1, wherein a methane-containing feedstock is used in stage (a) and the synthesis gas is produced by steam reforming, autothermal reforming, a combination of steam reforming and autothermal reforming, or by partial oxidation.

4. The process according to claim 1, wherein the synthesis gas comprises methane.

5. The process according to claim 1, wherein a copper- and zinc-containing heterogeneous catalyst is used as methanol synthesis catalyst in the methanol synthesis unit in step (b).

6. The process according to claim 1, wherein the methanol synthesis unit in step (b) comprises a compressor for compression of the synthesis gas, a reactor for conversion of the synthesis gas, a condenser for condensing out the crude methanol stream, and a conduit for recycling of uncondensed gas to the reactor.

7. The process according to claim 1, wherein in step (f), the carbon monoxide, carbon dioxide, dimethyl ether and methane components of value in the gaseous stream, the expansion gas, and the low boiler steam are fed to the combustion unit.

8. The process according to claim 1, wherein the oxygenous gas has an oxygen content of 90% to 100% by volume.

9. The process according to claim 1, wherein the combustion unit in step (f) comprises a combustion chamber and a condenser, water is condensed out of the combustion gas obtained in the combustion chamber in the condenser and conducted out of the combustion unit as a combustion output stream, and the remaining gaseous stream constitutes the carbon dioxide-containing flue gas.

10. The process according to claim 1, wherein, in the carbon dioxide recovery unit in step (g), carbon dioxide is absorbed from the carbon dioxide-containing flue gas in an absorber in a basic solvent to form the offgas stream, the carbon dioxide-enriched stream is released from the carbon dioxide-laden solvent in a desorber, and the carbon dioxide-depleted solvent is returned to the absorber.

11. The process according to claim 10, wherein the basic solvent used is an aqueous solution of an organic amine.

12. The process according to claim 11, wherein the organic amine used is monoethanolamine, piperazine, 2-amino-2-methyl-1-propanol, triethylenediamine, N-methyldiethanolamine or tert-butylaminoethoxyethanol.

13. The process according to claim 1, wherein, in step (h), the carbon dioxide-enriched stream (XIV) from step (g) is recycled to the methanol synthesis unit of step (b).

14. The process according to claim 1, wherein the carbon dioxide-enriched stream from step (g) comprises oxygen, and the carbon dioxide-enriched stream, before it is recycled to the synthesis gas production unit or to the methanol synthesis unit, is catalytically hydrogenated to deplete the oxygen.

15. The process according to claim 1, wherein, before the gaseous stream is fed to the combustion unit, hydrogen is separated off in a hydrogen recovery unit and recycled to the methanol synthesis unit of step (b).

16. The process according to claim 15, wherein the hydrogen is separated off by pressure swing adsorption in the hydrogen recovery unit.

17. The process according to claim 1, wherein the methanol synthesis unit in step (b) is supplied with further hydrogen in addition to the hydrogen supplied via the synthesis gas.

* * * * *